(12) United States Patent
Graham et al.

(10) Patent No.: US 8,921,394 B2
(45) Date of Patent: Dec. 30, 2014

(54) PROLYLCARBOXYPEPTIDASE INHIBITORS

(75) Inventors: Thomas H. Graham, Scotch Plains, NJ (US); Dong-Ming Shen, Edison, NJ (US); Min Shu, Green Brook, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/638,991

(22) PCT Filed: Apr. 21, 2011

(86) PCT No.: PCT/US2011/033347
§ 371 (c)(1),
(2), (4) Date: Oct. 2, 2012

(87) PCT Pub. No.: WO2011/137012
PCT Pub. Date: Nov. 3, 2011

(65) Prior Publication Data
US 2013/0030019 A1    Jan. 31, 2013

Related U.S. Application Data

(60) Provisional application No. 61/328,389, filed on Apr. 27, 2010.

(51) Int. Cl.
| | | |
|---|---|---|
| A01N 43/00 | (2006.01) |
| A61K 31/33 | (2006.01) |
| A01N 43/40 | (2006.01) |
| A61K 31/435 | (2006.01) |
| A61K 31/445 | (2006.01) |
| A61K 9/48 | (2006.01) |
| C07D 403/04 | (2006.01) |
| C07D 401/14 | (2006.01) |
| C07D 401/04 | (2006.01) |

(52) U.S. Cl.
CPC ............ *C07D 401/04* (2013.01); *A61K 9/4858* (2013.01); *C07D 403/04* (2013.01); *C07D 401/14* (2013.01)
USPC ............ 514/316; 514/183; 514/277; 514/322

(58) Field of Classification Search
None
See application file for complete search history.

(56) References Cited

U.S. PATENT DOCUMENTS

| 5,668,148 A * | 9/1997 | Payne et al. .................... 514/314 |
| 2008/0108080 A1 | 5/2008 | Chissoe |
| 2008/0269279 A1* | 10/2008 | Clements et al. ............ 514/302 |

FOREIGN PATENT DOCUMENTS

| EP | 1 498 424 A2 | 1/2005 |
| EP | 1 498 424 A3 | 5/2005 |
| WO | 94/26735 A1 | 11/1994 |
| WO | 02/068387 A2 | 9/2002 |
| WO | 02/068387 A3 | 9/2002 |
| WO | 2004/072265 A2 | 8/2004 |
| WO | 2004/072265 A3 | 8/2004 |
| WO | 2005/115446 A2 | 12/2005 |
| WO | 2005/115446 A3 | 12/2005 |
| WO | 2007/015157 A2 | 2/2007 |
| WO | 2007/015157 A3 | 2/2007 |
| WO | 2007/015162 A1 | 2/2007 |
| WO | 2007/140896 A1 | 12/2007 |
| WO | 2011/137024 A1 | 11/2011 |
| WO | 2011/143057 A1 | 11/2011 |
| WO | 2011/146300 A1 | 11/2011 |
| WO | 2011/146354 A1 | 11/2011 |
| WO | 2011/156220 A1 | 12/2011 |
| WO | 2011/156246 A1 | 12/2011 |

OTHER PUBLICATIONS

CAS RN: 191805-39-7 (entered Jul. 29, 1997).*
Rowley et al., "4-Heterocyclylpiperidines as Selective High-Affinity Ligands at the Human Dopamine D4 Receptor," J. Med. Chem. 1997, 40, 2374-2385.*
Rosenblum, J. S., Prolyl peptidases: a serine protease subfamily with high potential for drug discovery, Current Opinion in Chemical Biology, 2003, 496-504, 7, No. 4.
Bray, G A. et al., "Sibutramine Produces Dose-Related Weight Loss", Obesity Research, 1999, p. 189-, vol. 7, No. 2.
Davidson, M. H. et al., "Weight Control and Risk Factor Reduction in Obese Subjects Treated for 2 Years With Orlistat", JAMA, 1999, p. 235, vol. 281, No. 3.

(Continued)

*Primary Examiner* — Craig Ricci
*Assistant Examiner* — Jared D Barsky
(74) *Attorney, Agent, or Firm* — Baerbel R. Brown; Catherine D. Fitch

(57) ABSTRACT

Compounds of structural formula (I) are inhibitors of prolylcarboxypeptidase (PrCP). The compounds of the present invention are useful for the prevention and treatment of conditions related to the enzymatic activity of PrCP such as abnormal metabolism, including obesity; diabetes; metabolic syndrome; obesity related disorders; and diabetes related disorders.

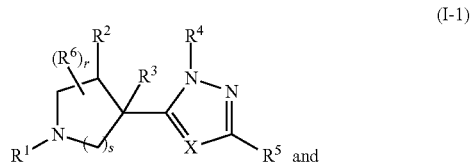

(I-1)

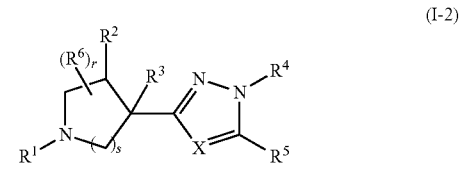

(I-2)

14 Claims, No Drawings

(56) References Cited

OTHER PUBLICATIONS

Douglas, A. et al., "Plasma Phentermine Levels, Weight Loss and Side-Effects", International Journal of Obesity, 1983, p. 591-595, vol. 7.

Encinosa, W. E. et al., "Recent Improvements in Bariatric Surgery Outcomes", Medical Care, 2009, p. 531-, vol. 47, No. 5.

Flum, D. R. et al., "Early Mortality Among Medicare Beneficiaries Undergoing Bariatric Surgical Procedures", JAMA, p. 1903-, vol. 294, No. 15.

Giraudo, S. Q. et al., "Feeding effects of hypothalamic injection of melanocortin 4 receptor ligands", Brain Research, 1998, p. 302-306, vol. 809.

Guy-Grand, B. et al., "International Trial of Long-Term Dexfenfluramine in Obesity", The Lancet, 1989, p. 1142-, vol. 2.

Kask, A. et al., "Selective Antagonist for the Melanocortin 4 Receptor (HS014) Increases Food Intake in Free-Feeding Rats", Biochemical and Biophysical Research Communications, 1998, p. 90-93, vol. 245.

Kopelman, P. G., "Obesity as a medical problem", Nature, 2000, p. 635-, vol. 404.

Vaisse, C. et al., "Melanocortin-4 receptor mutations are a frequent and heterogeneous cause of morbid obesity", The Journal of Clinical Investigation, 2000, p. 253-, vol. 106, No. 2.

Wallingford, N. et al., "Prolylcarboxypeptidase regulates food intake by inactivating a-MSH in rodents", The Journal of Clinical Investigation, 2009, p. 2291-, vol. 119. No. 8.

Williams, D. L. et al., "The melanocortin system as a central integrator of direct and indirect controls of food intake", Am. J. Physiol. Regul. Integr. Comp. Physiol, 2005, p. R2-R3, vol. 289.

* cited by examiner

PROLYLCARBOXYPEPTIDASE INHIBITORS

CROSS-REFERENCE TO RELATED APPLICATIONS

This application is a U.S. National Phase application under 35 U.S.C. §371 of PCT Application No. PCT/US2011/033347, filed 21 Apr. 2011, which claims priority from and the benefit of U.S. Provisional Application No. 61/328,389, filed Apr. 27, 2010.

FIELD OF THE INVENTION

The present invention relates to compounds which are inhibitors of the prolylcarboxy-peptidase (PrCP) enzyme and the use of such compounds to control, prevent and/or treat conditions or diseases mediated by prolylcarboxypeptidase activity. The compounds of the present invention are useful for the control, prevention and treatment of conditions and diseases related to abnormal metabolism, including obesity; diabetes; metabolic syndrome, obesity related disorders and diabetes related disorders.

BACKGROUND OF THE INVENTION

Obesity, which can be defined as a body weight more than 20% above the ideal body weight, is a major health concern in Western societies. It is estimated that about 97 million adults in the United States are overweight or obese. Obesity is the result of a positive energy balance, as a consequence of increased ratio of caloric intake to energy expenditure. Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include hypertension; type 2 diabetes mellitus; elevated plasma insulin concentrations; insulin resistance; dyslipidemias; hyperlipidemia; endometrial, breast, prostate and colon cancers; osteoarthritis; respiratory complications, such as obstructive sleep apnea; cholelithiasis; gallstones; arteriosclerosis; heart disease; abnormal heart rhythms; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death.

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," Brain Research, 80: 302-306 (1998)).

The prohormone pro-opiomelanocortin (POMC) plays a critical role in the regulations of energy metabolism, and is processed by proteases to produce several peptide hormones, including alpha-melanocyte-stimulating hormone ($\alpha$-MSH or $\alpha$-MSH$_{1-13}$). $\alpha$-MSH is a major regulator of feeding and body weight homeostasis. Studies have shown that $\alpha$-MSFI$_{1-13}$ is a critical anorexigenic neuromodulator found in the hypothalamus, which inhibits food intake by binding target neurons expressing melanocortin receptors 3 and 4 (MC3R and MC4R) (see Vaisse et al., J. Clin. Invest., 106, 253-62 (2000); and Williams et al., Am. J. Physiol. Regul. Integr. Comp. Physiol., 289:R2-R3 (2005). MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," Biochem. Biophys. Res. Commun., 245: 90-93 (1998)).

The enzyme prolylcarboxypeptidase (PRCP, Lysosomal Pro-X carboxypeptidase, angiotensinase C) is a serine protease that cleaves small, biologically active peptides at carboxyl termini linked to a penultimate proline group. $\alpha$-MSH is a substrate of PRCP due to its C-terminal amino acid sequence, Pro-Val. Recent studies have shown that PRCP initiates the degradation of $\alpha$-MSH$_{1-13}$ into inactive extracellular $\alpha$-MSH$_{1-12}$, which is effective in reducing food intake and in regulating neuronal functions via melanocortin receptors. In overnight fasted animals, 2.5 ug of $\alpha$-MSH$_{1-13}$ induced a 40% reduction in food intake relative to control animals, however, overnight fasted animals treated with 2.5 ug of $\alpha$-MSH$_{1-12}$ did not significantly affect food intake compared to the controls. (Wallingford et al., 3. Clinical Investigation, Vol. 119, No. 8, August 2009).

Further it has been shown that PRCP inhibition by small molecule protease inhibitors administered peripherally or centrally decreased food intake in wild type and genetically obese animals. Specifically, both the intracerebroventricular to rats and systemic administration to obese, leptin deficient mice of t-butyl carbamate-prolyl prolinal (BPP), which is an inhibitor of PRCP, resulted in a suppression of overnight food intake (Wallingford et al., J. Clinical Investigation, Vol. 119, No. 8, August 2009).

A recent study also showed that PrCP null mice had elevated hypothalamic levels of $\alpha$-MSH$_{1-13}$ and were leaner compared with wild-type controls when fed regular chow, and were also resistant to high fat diet induced obesity. Specifically, on a high fat diet, PrCP gt/gt mice also showed a significant reduction in body weight and a reduction in food intake (Wallingford et al., J. Clinical Investigation, Vol. 119, No. 8, August 2009).

These studies suggest that PRCP inhibitors influence food intake and weight maintenance via melanocortin receptors and the control of active $\alpha$-MSH$_{1-13}$ levels, and that targeting PRCP activity with central or peripheral administration of inhibitors can reduce food intake.

WO 2005/115446 discloses the role of prolylcarboxypeptidase inhibitors in weight control, control of body fat and food intake; and specific prolylcarboxypeptidase inhibitors, including t-butyl carbamate (BOC)-prolyl prolinal (BPP), N-benzyloxycarbonyl-prolyl-prolinal, diisopropyl fluorophosphates, PMSF, antipain, leupeptin, corn trypsin and mercuric chloride, useful to treat obesity and obesity related disorders. WO 2005/115446 also discloses the association of PRCP with hypertension, dyslipidemia, diabetes, stroke, gallbladder disease, cardiovascular disease, osteoarthritis, rheumatoid arthritis, hypercholesterolemia, angina, atherosclerosis, sleep apnea, respiratory problems, and cancer.

US 2008-0108080 discloses the utility of small molecule compounds with activity against the gene products encoded by PRCP for use in treating obesity.

WO 2007/140896 discloses the association of human PrCP with cardiovascular diseases, hematological diseases, neurological diseases and cancer based upon tissue distribution of PrCP.

The prolylcarboxypeptidase (PRCP) enzyme is disclosed in EP 1498424 and WO 2004/072265.

The present invention is concerned with novel spiroether compounds as inhibitors of prolylcarboxypeptidase which are useful in the treatment and/or prevention of various conditions and diseases mediated by prolylcarboxypeptidase activity including, but not limited to, abnormal metabolism, obesity, diabetes, metabolic syndrome, obesity and diabetes related disorders, such as hypertension, dyslipidemia, stroke, gallbladder disease, cardiovascular disease, osteoarthritis, rheumatoid arthritis, hypercholesterolemia, stable angina, unstable angina, artherosclerosis, sleep apnea, respiratory problems, cancer, stroke, hematological diseases and neurological diseases.

Weight loss drugs that are currently used to treat obesity have limited efficacy and significant side effects. Studies of the weight loss medications orlistat (Davidson, M. H. et al. (1999) JAMA 281:235-42), dexfenfluramine (Guy Grand, B. et al. (1989) Lancet 2:1142-5), sibutramine (Bray, G. A. et al. (1999) Obes. Res. & 189-98) and phentermine (Douglas, A. et al. (1983) Int. J. Obes. 7:591-5) have demonstrated a limited weight loss of about 5%-10% of body weight for drug compared to placebo. The side effects of these drugs and anti-obesity agents further limit their use. Dexfenfluramine was withdrawn from the market because of suspected heart valvulopathy; orlistat is limited by gastrointestinal side effects; the use of topiramate is limited by central nervous system effects; and the use of sibutramine is limited by its cardiovascular side effects which have led to reports of deaths and its withdrawal from the market in Italy. Obese patients generally respond well to surgical interventions that modify the gastrointestinal tract and limit food intake. However, one out of fifty bariatric surgery patients dies within the first 30 days post surgery, and 4.6% of bariatric surgery patients die within the first year (*J. Amer. Med. Assoc.*, 2005, 294, 1903). Another study indicated that 33% of patients that undergo bariatric surgery have complications that require re-hospitalization within the first 6 months post operation (*Medical Care*, 2009, 47, 531).

There is a need for a weight loss treatment with enhanced efficacy, increased safety, and fewer undesirable side effects. The instant invention addresses this problem by providing prolylcarboxypeptidase inhibitors useful in the treatment and prevention of obesity, diabetes, and related disorders.

SUMMARY OF THE INVENTION

The present invention relates to compounds of structural formulas I-1 and I-2:

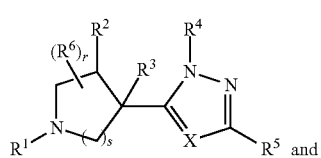
(I-1)

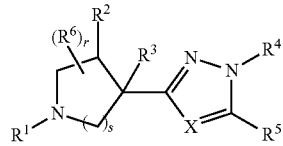
(I-2)

Compounds of formula I are inhibitors of prolylcarboxypeptidase (PrCP) and as such are useful in the treatment, control or prevention of diseases, disorders or conditions responsive to the modulation of the prolylcarboxypeptidase (PrCP) enzyme. In particular, the compounds of formula I act as inhibitors of the prolylcarboxypeptidase (PrCP) enzyme useful in the treatment, control or prevention of diseases, disorders or conditions responsive to the inhibition of prolylcarboxypeptidase (PRCP), such as eating disorders due to excessive food intake, and the resulting obesity and complications associated therewith, including diabetes, obesity related disorders and diabetes related disorders.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of prolylcarboxypeptidase in a subject in need thereof by administering the compounds and pharmaceutical compositions of the present invention.

The present invention also relates to methods for the treatment, control, or prevention of obesity, Type 2 diabetes, metabolic syndrome, obesity related disorders and diabetes related disorders by administering the compounds and pharmaceutical compositions of the present invention.

DETAILED DESCRIPTION OF THE INVENTION

The present invention is concerned with compounds useful as inhibitors of prolylcarboxypeptidase. The compounds of the present invention are described by structural formulas I-1 and I-2:

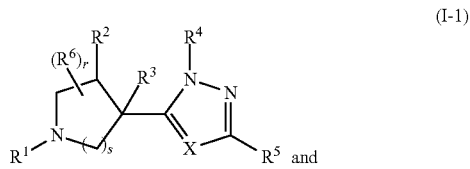
(I-1)

and

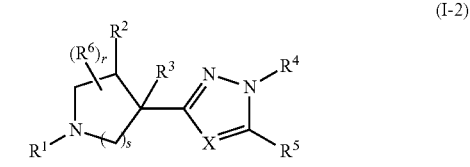
(I-2)

or a pharmaceutically acceptable salt thereof; wherein
X is CH or N;
each $R^1$ is independently selected from the group consisting of:
(1) hydrogen,
(2) —$C_{1-6}$ alkyl,
(3) —$C_{1-6}$ alkoxy,
(4) —$(CH_2)_m CO_2 C_{1-6}$ alkyl,
(5) —$(CH_2)_m COC_{1-6}$ alkyl,
(6) —$(CH_2)_m$—C(O)—$(CH_2)_u$-halogen, (7) —(CH$_2$)$_m$—C(O)—(CH$_2$)$_u$CO$_2$H,
(8) —(CH$_2$)$_m$—C(O)—(CH$_2$)$_n$CO$_2$C$_{1-6}$ alkyl,
(9) —(CH$_2$)$_m$—C(O)—(CH$_2$)$_p$N(R$^e$)$_2$,
(10) —(CH$_2$)$_m$—C(O)—(CH$_2$)$_p$—C$_{3-6}$cycloalkyl,
(11) —(CH$_2$)$_m$—C(O)—(CH$_2$)$_p$—C$_{2-6}$cycloheteroalkyl,
(12) —(CH$_2$)$_m$—C(O)—(CH$_2$)$_p$-aryl,
(13) —(CH$_2$)$_m$—C(O)—(CH$_2$)$_p$-heteroaryl,
(14) —(CH$_2$)$_m$—CH(OH)—(CH$_2$)$_p$—C$_{3-6}$cycloalkyl,
(15) —(CH$_2$)$_m$—CH(OH)—(CH$_2$)$_p$—C$_{2-6}$cycloheteroalkyl,
(16) —(CH$_2$)$_m$—CH(OH)—(CH$_2$)$_p$-aryl,
(17) —(CH$_2$)$_m$—CH(OH)—(CH$_2$)$_p$-heteroaryl,
(18) —(CH$_2$)$_m$—NR$^e$—C$_{1-6}$ alkyl,
(19) —(CH$_2$)$_m$—O—C$_{1-6}$ alkyl,
(20) —(CH$_2$)$_m$—S—C$_{1-6}$ alkyl,
(21) —(CH$_2$)$_m$—SO$_2$—C$_{1-6}$ alkyl,
(22) —(CH$_2$)$_m$—SO$_2$-aryl,
(23) —(CH$_2$)$_m$ C$_{3-7}$cycloalkyl,
(24) —(CH$_2$)$_m$ C$_{2-6}$cycloheteroalkyl,
(25) —(CH$_2$)$_m$ aryl, and
(26) —(CH$_2$)$_m$ heteroaryl,
wherein each CH$_2$, alkyl, alkoxy, cycloalkyl, cycloheteroalkyl, aryl and heteroaryl is unsubstituted or substituted with one to three groups independently selected from R$^a$;
each R$^2$ is independently selected from the group consisting of:
  (1) hydrogen,
  (2) —C$_{1-6}$ alkyl,
  (3) —C$_{1-6}$ alkoxy,
  (4) —(CH$_2$)$_n$ C$_{3-7}$cycloalkyl,
  (5) —(CH$_2$)$_n$ C$_{2-6}$cycloheteroalkyl,
  (6) —(CH$_2$)$_n$ aryl, and
  (7) —(CH$_2$)$_n$ heteroaryl,
wherein each CH$_2$, alkyl, alkoxy, cycloalkyl, cycloheteroalkyl, aryl and heteroaryl is unsubstituted or substituted with one, two or three substituents selected from R$^b$; each R$^3$ is independently selected from the group consisting of:
  (1) hydrogen,
  (2) —C$_{1-6}$ alkyl,
  (3) —C$_{1-6}$ alkoxy,
  (4) —(CH$_2$)$_q$ C$_{3-7}$cycloalkyl,
  (5) —(CH$_2$)$_q$ C$_{2-6}$cycloheteroalkyl,
  (6) —(CH$_2$)$_q$ aryl, and
  (7) —(CH$_2$)$_q$ heteroaryl,
wherein each CH$_2$, alkyl, alkoxy, cycloalkyl, cycloheteroalkyl, aryl and heteroaryl is unsubstituted or substituted with one to three substituents selected from R$^c$, provided that at least one of R$^2$ and R$^3$ is not hydrogen;
each R$^4$ is independently selected from the group consisting of:
  (1) hydrogen, and
  (2) —C$_{1-6}$ alkyl,
wherein alkyl is unsubstituted or substituted with hydroxy or one to three halogens;
each R$^5$ is independently selected from the group consisting of:
  (1) hydrogen,
  (2) —C$_{1-6}$ alkyl,
  (3) —C$_{1-6}$ alkoxy,
  (4) —CF$_3$,
  (5) —(CH$_2$)$_t$ C$_{3-7}$cycloalkyl,
  (6) —(CH$_2$)$_t$ C$_{2-6}$cycloheteroalkyl,
  (7) —(CF$_{12}$)$_t$ aryl, and
  (8) —(CH$_2$)$_t$ heteroaryl,
wherein each CH$_2$, alkyl, alkoxy, cycloalkyl, cycloheteroalkyl, aryl and heteroaryl is unsubstituted or substituted with one to three substituents selected from R$^d$;

each R$^6$ is independently selected from the group consisting of:
  (1) hydrogen,
  (2) halogen,
  (3) —CF$_3$, and
  (4) —C$_{1-6}$ alkyl,
wherein alkyl is unsubstituted or substituted with hydroxy or one to three halogens; each R$^a$ is independently selected from the group consisting of:
  (1) hydrogen,
  (2) oxo,
  (3) halogen,
  (4) —C$_{1-4}$alkyl,
  (5) —OC$_{1-4}$alkyl,
  (6) —CF$_3$,
  (7) —OH,
  (8) —OCF$_3$,
  (9) —CN, and
  (10) —CO$_2$—C$_{1-6}$alkyl;
each R$^b$ is independently selected from the group consisting of:
  (1) hydrogen,
  (2) halogen,
  (3) —C$_{1-4}$alkyl,
  (4) —OC$_{1-4}$alkyl,
  (5) —CF$_3$,
  (6) —OCF$_3$,
  (7) —CN, and
  (8) —CO$_2$—C$_{1-6}$alkyl;
R$^c$ is independently selected from the group consisting of:
  (1) hydrogen,
  (2) halogen,
  (3) —C$_{1-4}$alkyl,
  (4) —OC$_{1-4}$alkyl,
  (5) —CF$_3$,
  (6) —OCF$_3$,
  (7) —CN, and
  (8) —CO$_2$—C$_{1-6}$alkyl;
each R$^d$ is independently selected from the group consisting of:
  (1) hydrogen,
  (2) halogen,
  (3) —C$_{1-4}$alkyl,
  (4) —OC$_{1-4}$alkyl,
  (5) —CF$_3$,
  (6) —OCF$_3$,
  (7) —CN, and
  (8) —CO$_2$—C$_{1-6}$alkyl;
each R$^e$ is independently selected from the group consisting of:
  (1) hydrogen, and
  (2) —C$_{1-6}$ alkyl;
m is selected from 0, 1, 2 and 3;
n is selected from 0, 1, 2, and 3;
p is selected from 0, 1, 2 and 3;
q is selected from 0, 1, 2 and 3;
r is selected from 0, 1, and 2;
s is selected from 1 and 2;
t is selected from 0, 1, 2 and 3; and
u is selected from 1, 2 and 3.

In one embodiment of the present invention, X is CH or N. In another embodiment of the present invention, X is CH. In another embodiment of the present invention, X is N.

In another embodiment of the present invention, each R$^1$ is independently selected from the group consisting of: hydrogen, —C$_{1-6}$ alkyl, —C$_{1-6}$ alkoxy, —(CH$_2$)$_m$CO$_2$C$_{1-6}$ alkyl, —(CH$_2$)$_m$COC$_{1-6}$ alkyl, —(CH$_2$)$_m$—C(O)—(CH$_2$)$_u$-halogen, —(CH$_2$)$_m$—C(O)—(CH$_2$)$_u$CO$_2$H, —(CH$_2$)$_m$—C(O)—(CH$_2$)$_u$CO$_2$C$_{1-6}$ alkyl, —(CH$_2$)$_m$—C(O)—(CH$_2$)$_p$N(R$^e$)$_2$, —(CH$_2$)$_m$—C(O)—(CH$_2$)$_p$—C$_{3-6}$cycloalkyl, —(CH$_2$)$_m$—C(O)—(CH$_2$)$_p$—C$_{2-6}$cycloheteroalkyl, —(CH$_2$)$_m$—C(O)—(CH$_2$)$_p$-aryl, —(CH$_2$)$_m$—C(O)—(CH$_2$)$_p$-heteroaryl, —(CH$_2$)$_m$—CH(OH)—(CH$_2$)$_p$—C$_{3-6}$cycloalkyl, —(CH$_2$)$_m$—CH(OH)—(CH$_2$)$_p$—C$_{2-6}$cycloheteroalkyl, —(CH$_2$)$_m$—CH(OH)—(CH$_2$)$_p$-aryl, —(CH$_2$)$_m$—CH(OH)—(CH$_2$)$_p$-heteroaryl, —(CH$_2$)$_m$—NR$^e$—C$_{1-6}$ alkyl, —(CH$_2$)$_m$—O—C$_{1-6}$ alkyl, —(CH$_2$)$_m$—S—C$_{1-6}$ alkyl, —(CH$_2$)$_m$—SO$_2$—C$_{1-6}$ alkyl, —(CH$_2$)$_m$—SO$_2$-aryl, —(CH$_2$)$_m$ C$_{3-7}$cycloalkyl, —(CH$_2$)$_m$ C$_{2-6}$cycloheteroalkyl, —(CH$_2$)$_m$ aryl and —(CH$_2$)$_m$ heteroaryl, wherein each CH$_2$, alkyl, alkoxy, cycloalkyl, cycloheteroalkyl, aryl and heteroaryl is unsubstituted or substituted with one to three groups independently selected from R$^a$.

In another embodiment of the present invention, each R$^1$ is independently selected from the group consisting of: hydrogen, —C$_{1-6}$ alkyl, —(CH$_2$)$_m$—C(O)-aryl, —(CH$_2$)$_m$—CH(OH)—(CH$_2$)$_p$-aryl, —(CH$_2$)$_m$—SO$_2$-aryl, —(CH$_2$)$_m$ C$_{2-6}$cycloheteroalkyl, —(CH$_2$)$_m$ aryl, and —(CH$_2$)$_m$ heteroaryl, wherein each CH$_2$, alkyl, cycloheteroalkyl, aryl and heteroaryl is unsubstituted or substituted with one to three groups independently selected from R$^a$.

In a class of this embodiment, each R$^1$ is independently selected from the group consisting of hydrogen, —C$_{1-6}$ alkyl, —(CH$_2$)$_m$—C(O)-phenyl, —(CH$_2$)$_m$—CH(OH)—(CH$_2$)$_p$-phenyl, —(CH$_2$)$_m$—SO$_2$-phenyl, —(CH$_2$)$_m$-piperidine, —(CH$_2$)$_m$ phenyl, and —(CH$_2$)$_m$ pyridine, wherein each CH$_2$, alkyl, piperidine, phenyl and pyridine is unsubstituted or substituted with one to three groups independently selected from R$^a$. In another class of this embodiment, each R$^1$ is independently selected from the group consisting of: hydrogen, —CH$_2$C(CH$_3$)$_3$, —C(CH$_3$)$_3$, —CH(CH$_3$)$_2$, —CH$_2$CF$_3$, —(CH$_2$)$_2$CF$_3$, —CH$_2$—C(O)-phenyl, —CH$_2$—CH(OH)-phenyl, —SO$_2$-phenyl, piperidine, —(CH$_2$)$_2$-phenyl, CH$_2$-phenyl, —(CH$_2$)-pyridine, and pyridine, wherein each CH$_2$, alkyl, piperidine, phenyl and pyridine is unsubstituted or substituted with one to three groups independently selected from R$^a$.

In another embodiment of the present invention, each R$^1$ is independently selected from the group consisting of: —C$_{1-6}$ alkyl, and —(CH$_2$)$_{1n}$ aryl, wherein each CH$_2$, alkyl and aryl is unsubstituted or substituted with one to three groups independently selected from R$^a$.

In a class of this embodiment, each R$^1$ is independently selected from the group consisting of: —C$_{1-6}$ alkyl, and —(CH$_2$)$_m$ phenyl, wherein each CH$_2$, alkyl and phenyl is unsubstituted or substituted with one to three groups independently selected from R$^a$. In a subclass of this class, each R$^1$ is independently selected from the group consisting of: —C$_{1-6}$ alkyl, and —(CH$_2$)$_m$ phenyl, wherein each CH$_2$, alkyl and phenyl is unsubstituted or substituted with one group independently selected from R$^a$. In another subclass of this class, each R$^1$ is independently selected from the group consisting of: —CH$_2$C(C$_{1-13}$)$_3$, —C(CH$_3$)$_3$, and —(CH$_2$)$_2$-phenyl, wherein each CH$_2$, alkyl and phenyl is unsubstituted or substituted with one or two groups independently selected from R$^a$. In a subclass of this subclass, each R$^1$ is independently selected from the group consisting of: —CH$_2$C(CH$_3$)$_3$, —C(CH$_3$)$_3$, and —(CH$_2$)$_2$-phenyl, wherein each CH$_2$, alkyl and phenyl is unsubstituted or substituted with one group independently selected from R$^a$.

In another embodiment of the present invention, each R$^2$ is independently selected from the group consisting of: hydrogen, —C$_{1-6}$ alkyl, —C$_{1-6}$ alkoxy, —(CH$_2$)$_n$ C$_{3-7}$cycloalkyl, —(CH$_2$)$_n$ C$_{2-6}$cycloheteroalkyl, —(CH$_2$)$_n$ aryl, and —(CH$_2$)$_n$ heteroaryl, wherein each CH$_2$, alkyl, alkoxy, cycloalkyl, cycloheteroalkyl, aryl and heteroaryl is unsubstituted or substituted with one, two or three substituents selected from R$^b$.

In a class of this embodiment, each R$^2$ is independently selected from the group consisting of: hydrogen, and —(CH$_2$)$_n$ aryl, wherein each CH$_2$, and aryl is unsubstituted or substituted with one or two substituents selected from R$^b$. In a subclass of this class, each R$^2$ is independently selected from the group consisting of: hydrogen, and —(CH$_2$)$_n$ phenyl, wherein each CH$_2$ and phenyl is unsubstituted or substituted with one or two substituents selected from R$^b$. In another class of this embodiment, each R$^2$ is independently selected from the group consisting of: hydrogen, and -aryl, wherein each CH$_2$, and aryl is unsubstituted or substituted with one or two substituents selected from R$^b$. In a subclass of this class, each R$^2$ is independently selected from the group consisting of: hydrogen, and -phenyl, wherein each phenyl is unsubstituted or substituted with one or two substituents selected from R$^b$.

In another embodiment of the present invention, each R$^3$ is independently selected from the group consisting of: hydrogen, —C$_{1-6}$ alkyl, —C$_{1-6}$ alkoxy, —(CH$_2$)$_q$ C$_{3-7}$cycloalkyl, —(CH$_2$)$_q$C$_{2-6}$cycloheteroalkyl, —(CH$_2$)$_q$ aryl, and —(CH$_2$)$_q$ heteroaryl, wherein each CH$_2$, alkyl, alkoxy, cycloalkyl, cycloheteroalkyl, aryl and heteroaryl is unsubstituted or substituted with one to three substituents selected from R$^c$, provided that at least one of R$^2$ and R$^3$ is not hydrogen. In a class of this embodiment, each R$^3$ is independently selected from the group consisting of: hydrogen, C$_{1-6}$ alkyl, —(CH$_2$)$_q$ aryl, and —(CH$_2$)$_q$ heteroaryl, wherein each CH$_2$, alkyl, aryl and heteroaryl is unsubstituted or substituted with one to three substituents selected from R$^c$, provided that at least one of R$^2$ and R$^3$ is not hydrogen. In another class of this embodiment, each R$^3$ is independently selected from the group consisting of: hydrogen, —C$_{1-6}$ alkyl, -aryl, and -heteroaryl, wherein each alkyl, aryl and heteroaryl is unsubstituted or substituted with one to three substituents selected from R$^c$, provided that at least one of R$^2$ and R$^3$ is not hydrogen. In another class of this embodiment, each R$^3$ is independently selected from the group consisting of: hydrogen, —C$_{1-6}$ alkyl, -phenyl, and -pyridine, wherein each alkyl, phenyl and pyridine is unsubstituted or substituted with one to three substituents selected from R$^c$, provided that at least one of R$^2$ and R$^3$ is not hydrogen. In another class of this embodiment, each R$^3$ is independently selected from the group consisting of: hydrogen, —CH$_3$, —CH$_2$CH$_3$, -phenyl, and -pyridine, wherein each alkyl, phenyl and pyridine is unsubstituted or substituted with one to three substituents selected from R$^c$, provided that at least one of R$^2$ and R$^3$ is not hydrogen.

In another embodiment of the present invention, each R$^3$ is independently selected from the group consisting of: hydrogen, -aryl, and -heteroaryl, wherein each CH$_2$, alkyl, aryl and heteroaryl is unsubstituted or substituted with one to three substituents selected from R$^c$, provided that at least one of R$^2$ and R$^3$ is not hydrogen. In a class of this embodiment, each R$^3$ is independently selected from the group consisting of: hydrogen, -phenyl, and -pyridine, wherein each phenyl and pyridine is unsubstituted or substituted with one to three substituents selected from R$^c$, provided that at least one of R$^2$ and R$^3$ is not hydrogen. In another class of this embodiment, each R$^3$ is independently selected from the group consisting of: hydrogen, -phenyl, and -pyridine, wherein each phenyl and pyridine is =substituted or substituted with one substituent selected from R$^c$, provided that at least one of R$^2$ and R$^3$ is not hydrogen.

In another embodiment of the present invention, $R^4$ is selected from the group consisting of: hydrogen, and —$C_{1-6}$ alkyl, wherein alkyl is =substituted or substituted with hydroxy or one to three halogens. In a class of this embodiment, $R^4$ is selected from the group consisting of: hydrogen, and —$CH_3$. In another class of this embodiment, $R^4$ is hydrogen. In another class of this embodiment, $R^4$ is —$C_{1-6}$ alkyl, wherein alkyl is unsubstituted or substituted with hydroxy or one to three halogens. In another class of this embodiment, $R^4$ is —$C_{1-6}$ alkyl. In another class of this embodiment, $R^4$ is —$CH_3$.

In another embodiment of the present invention, $R^5$ is selected from the group consisting of: hydrogen, —$C_{1-6}$ alkyl, —$C_{1-6}$ alkoxy, —$CF_3$, —$(CH_2)_t$ $C_{3-7}$cycloalkyl, —$(CH_2)_t$ $C_{2-6}$cycloheteroalkyl, —$(CH_2)_t$ aryl, and —$(CH_2)_t$ heteroaryl, wherein each $CH_2$, alkyl, alkoxy, cycloalkyl, cycloheteroalkyl, aryl and heteroaryl is unsubstituted or substituted with one to three substituents selected from $R^d$. In a class of this embodiment, $R^5$ is selected from the group consisting of: —$C_{1-6}$ alkyl, —$CF_3$, and —$(CH_2)_t$ aryl, wherein each $CH_2$, alkyl and aryl is unsubstituted or substituted with one to three substituents selected from $R^d$. In a subclass of this class, $R^5$ is selected from the group consisting of —$CH_3$, —$C(CH_3)_3$, —$CF_3$, —$(CH_2)_2$-phenyl, and -phenyl, wherein each $CH_2$, alkyl and phenyl is unsubstituted or substituted with one to three substituents selected from $R^d$. In another class of this embodiment, $R^5$ is selected from the group consisting of: —$(CH_2)_t$ aryl, wherein each $CH_2$ and aryl is unsubstituted or substituted with one to three substituents selected from $R^d$. In a subclass of this class, $R^5$ is selected from the group consisting of: —$(CH_2)_t$ phenyl, wherein each $CH_2$ and phenyl is unsubstituted or substituted with one to three substituents selected from $R^d$. In another subclass of this class, $R^5$ is selected from the group consisting of: —$(CH_2)_t$ phenyl, wherein each $CH_2$ and phenyl is unsubstituted or substituted with one to three substituents selected from $R^d$; and t is 0 or 2. In another subclass of this class, $R^5$ is selected from the group consisting of: —$(CH_2)_2$-phenyl, and -phenyl, wherein each $CH_2$ and phenyl is unsubstituted or substituted with one to three substituents selected from $R^d$. In another subclass of this class, $R^5$ is —$(CH_2)_2$-phenyl, wherein each $CH_2$ and phenyl is unsubstituted or substituted with one to three substituents selected from $R^d$. In another subclass of this class, $R^5$ is -phenyl, wherein phenyl is unsubstituted or substituted with one to three substituents selected from $R^d$.

In another embodiment of the present invention, each $R^6$ is independently selected from the group consisting of: hydrogen, halogen, —$CF_3$, and —$C_{1-6}$ alkyl, wherein alkyl is unsubstituted or substituted with hydroxy or one to three halogens. In a class of this embodiment, each $R^6$ is independently selected from the group consisting of: hydrogen, and halogen. In another class of this embodiment, each $R^6$ is independently selected from the group consisting of: hydrogen, and F. In another class of this embodiment, $R^6$ is hydrogen. In another class of this embodiment, $R^6$ is halogen.

In another embodiment of the present invention, each $R^a$ is independently selected from the group consisting of: hydrogen, oxo, halogen, —$C_{1-4}$alkyl, —$OC_{1-4}$alkyl, —$CF_3$, —OH, —$OCF_3$, —CN, and —$CO_2$—$C_{1-6}$alkyl. In a class of this embodiment, each $R^a$ is independently selected from the group consisting of: hydrogen, oxo, halogen, —$CF_3$, —OH, —$OCF_3$, —CN, and —$CO_2$—$C_{1-6}$alkyl. In a subclass of this class, each $R^a$ is independently selected from the group consisting of: hydrogen, oxo, F, Cl, Br, —$CF_3$, —OH, —$OCF_3$, —CN, and —$C(O)OC(CH_3)_3$. In another class of this embodiment, each $R^a$ is independently selected from the group consisting of: oxo, halogen, —$CF_3$, —OH, —$OCF_3$, —CN, and —$CO_2$—$C_{1-6}$alkyl. In a subclass of this class, each $R^a$ is independently selected from the group consisting of oxo, F, Cl, Br, —$CF_3$, —OH, —$OCF_3$, —CN, and —$C(O)OC(CH_3)_3$. In another class of this embodiment, $R^a$ is halogen. In a subclass of this class, $R^a$ is selected from the group consisting of: F, Cl, and Br. In another subclass of this class, $R^a$ is F. In another subclass of this class, $R^a$ is Cl. In another subclass of this class, $R^a$ is Br.

In another embodiment of the present invention, each $R^b$ is independently selected from the group consisting of: hydrogen, halogen, —$C_{1-4}$alkyl, —$OC_{1-4}$alkyl, —$CF_3$, —$OCF_3$, —CN, and —$CO_2$—$C_{1-6}$alkyl. In a class of this embodiment, each $R^b$ is independently selected from the group consisting of: hydrogen, F, Cl, Br, —$C_{1-4}$alkyl, —$OC_{1-4}$alkyl, —$CF_3$, —$OCF_3$, —CN, and —$C(O)OC(CH_3)_3$. In another embodiment of the present invention, $R^b$ is hydrogen or halogen. In a class of this embodiment, $R^b$ is hydrogen, F, Cl, or Br. In another class of this embodiment, $R^b$ is halogen. In a subclass of this class, $R^b$ is F, Cl, or Br. In another subclass of this class, $R^b$ is F. In another subclass of this class, $R^b$ is Cl. In another subclass of this class, $R^b$ is Br.

In another embodiment of the present invention, each $R^c$ is independently selected from the group consisting of: hydrogen, halogen, —$C_{1-4}$alkyl, —$C_{1-4}$alkyl, —$CF_3$, —$OCF_3$, —CN, and —$CO_2$—$C_{1-6}$alkyl. In a class of this embodiment, each $R^d$ is independently selected from the group consisting of: hydrogen, F, Cl, Br, —$C_{1-4}$alkyl, —$OC_{1-4}$alkyl, —$CF_3$, —$OCF_3$, —CN, and —$C(O)OC(CH_3)_3$. In another embodiment of the present invention, each $R^c$ is independently selected from the group consisting of: hydrogen, halogen, and —$C_{1-4}$alkyl. In a class of this embodiment, each $R^c$ is independently selected from the group consisting of: hydrogen, F, Cl, Br, and —$C_{1-4}$alkyl. In another class of this embodiment, $R^c$ is hydrogen.

In another embodiment of the present invention, each $R^d$ is independently selected from the group consisting of: hydrogen, halogen, —$C_{1-4}$alkyl, —$CF_3$, —$OCF_3$, —CN, and —$CO_2$—$C_{1-6}$alkyl. In a class of this embodiment, each $R^d$ is independently selected from the group consisting of: hydrogen, F, Cl, Br, —$C_{1-4}$alkyl, —$OC_{1-4}$alkyl, —$CF_3$, —$OCF_3$, —CN, and —$C(O)OC(CH_3)_3$.

In another embodiment of the present invention, each $R^d$ is independently selected from the group consisting of: halogen, and —CN. In a class of this embodiment, each $R^d$ is independently selected from the group consisting of: F, Cl, Br, and —CN. In another class of this embodiment, each $R^d$ is independently selected from the group consisting of: F, Cl, and —CN.

In another embodiment of the present invention, $R^e$ is selected from the group consisting of: hydrogen, and —$C_{1-6}$ alkyl. In a class of this embodiment, $R^e$ is selected from the group consisting of hydrogen, and —$CH_3$. In another class of this embodiment, $R^e$ is hydrogen. In another class of this embodiment, $R^e$ is —$C_{1-6}$ alkyl. In another class of this embodiment, $R^e$ is —$CH_3$.

In another embodiment of the present invention, m is 0, 1, 2, or 3. In a class of this embodiment, m is 0, 1 or 2. In another class of this embodiment, m is 0 or 1. In another class of this embodiment, m is 0 or 2. In another class of this embodiment, m is 1 or 2. In another class of this embodiment, m is 0. In another class of this embodiment, m is 1. In another class of this embodiment, m is 2. In another class of this embodiment, m is 3.

In another embodiment of the present invention, n is 0, 1, 2, or 3. In a class of this embodiment, n is 0, 1 or 2. In another class of this embodiment, n is 0 or 1. In another class of this embodiment, n is 0 or 2. In another class of this embodiment, n is 1 or 2. In another class of this embodiment, n is 0. In another class of this embodiment, n is 1. In another class of this embodiment, n is 2. In another class of this embodiment, n is 3.

In another embodiment of the present invention, p is 0, 1, 2, or 3. In a class of this embodiment, p is 0, 1 or 2. In another class of this embodiment, p is 0 or 1. In another class of this embodiment, p is 0 or 2. In another class of this embodiment, p is 1 or 2. In another class of this embodiment, p is 0. In another class of this embodiment, p is 1. In another class of this embodiment, p is 2. In another class of this embodiment, p is 3.

In another embodiment of the present invention, q is 0, 1, 2, or 3. In a class of this embodiment, q is 0, 1 or 2. In another class of this embodiment, q is 0 or 1. In another class of this embodiment, q is 0 or 2. In another class of this embodiment, q is 1 or 2. In another class of this embodiment, q is 0. In another class of this embodiment, q is 1. In another class of this embodiment, q is 2. In another class of this embodiment, q is 3.

In another embodiment of the present invention, r is 0, 1, or 2. In a class of this embodiment, r is 0 or 1. In another class of this embodiment, r is 0 or 2. In another class of this embodiment, r is 1 or 2. In another class of this embodiment, r is 0. In another class of this embodiment, r is 1. In another class of this embodiment, r is 2.

In another embodiment of the present invention, s is 1 or 2. In another class of this embodiment, s is 1, In another class of this embodiment, s is 2.

In another embodiment of the present invention, t is 0, 1, 2, or 3. In a class of this embodiment, t is 0, 1 or 2. In another class of this embodiment, t is 0 or 1. In another class of this embodiment, t is 1 or 2. In another class of this embodiment, t is 0 or 2. In another class of this embodiment, t is 0. In another class of this embodiment, t is 1. In another class of this embodiment, t is 2. In another class of this embodiment, t is 3.

In another embodiment of the present invention, u is 1, 2, or 3. In a class of this embodiment, u is 1 or 2. In another class of this embodiment, u is 1 or 3. In another class of this embodiment, u is 2 or 3. In another class of this embodiment, u is 1. In another class of this embodiment, u is 2. In another class of this embodiment, u is 3.

In another embodiment of the present invention, the invention relates to compounds of structural formula I-1 and I-2 wherein:

$R^1$ is selected from the group consisting of:
(1) hydrogen,
(2) —$C_{1-6}$ alkyl,
(3) —$(CH_2)_m$—C(O)-aryl,
(4) —$(CH_2)_m$—CH(OH)—$(CH_2)_p$-aryl,
(5) —$(CH_2)_m$—$SO_2$-aryl,
(6) —$(CH_2)_m$ $C_{2-6}$cycloheteroalkyl,
(7) —$(CH_2)_m$ aryl, and
(8) —$(CH_2)_m$ heteroaryl,
wherein each $CH_2$, alkyl, cycloheteroalkyl, aryl and heteroaryl is unsubstituted or substituted with one to three groups independently selected from $R^a$;
$R^2$ is selected from the group consisting of
(1) hydrogen, and
(2) —$(CH_2)_n$ aryl,
wherein each $CH_2$, and aryl is unsubstituted or substituted with one or two substituents selected from $R^b$;
$R^3$ is selected from the group consisting of:
(1) hydrogen,
(2) —$C_{1-6}$ alkyl,
(3) -aryl, and
(4)-heteroaryl, wherein each alkyl, aryl and heteroaryl is unsubstituted or substituted with one to three substituents selected from $R^c$, provided that at least one of $R^2$ and $R^3$ is not hydrogen; $R^5$ is —$(CH_2)_t$ phenyl, wherein each $CH_2$ and phenyl is unsubstituted or substituted with one to three substituents selected from $R^d$;
$R^6$ is hydrogen; and
m is 0, 1 or 2;
n is 0 or 1;
p is 0 or 1; and
t is 0 or 2;
or a pharmaceutically acceptable salt thereof.

In another embodiment of the present invention, the invention relates to compounds of structural formula I-1 or 1-2 wherein:
$R^1$ is independently selected from the group consisting of:
(1) —$C_{1-6}$ alkyl, and
(2) —$(CH_2)_m$ phenyl,
wherein each $CH_2$, alkyl and phenyl is unsubstituted or substituted with one to three groups independently selected from $R^a$;
$R^2$ is selected from the group consisting of:
(1) hydrogen, and
(2) -phenyl,
wherein each phenyl is unsubstituted or substituted with one or two substituents selected from $R^b$;
$R^3$ is selected from the group consisting of:
(1) hydrogen,
(2) -phenyl, and
(3) -pyridine,
wherein each phenyl and pyridine is unsubstituted or substituted with one to three substituents selected from $R^c$, provided that at least one of $R^2$ and $R^3$ is not hydrogen;
$R^5$ is selected from the group consisting of:
(1) —$(CH_2)_2$-phenyl, and
(2) -phenyl,
wherein each $CH_2$ and phenyl is unsubstituted or substituted with one to three substituents selected from $R^d$;
$R^6$ is hydrogen; and
m is 2;
or a pharmaceutically acceptable salt thereof.

In another embodiment of the present invention, the invention relates to compounds of structural formulas Ia-1 and Ia-2:

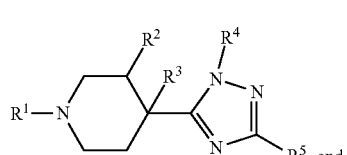

Ia-1 and

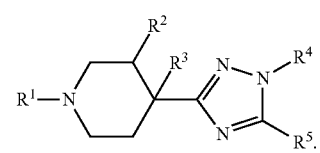

Ia-2

In another embodiment of the present invention, the invention relates to compounds of structural formula Ib-1 and Ib-2:

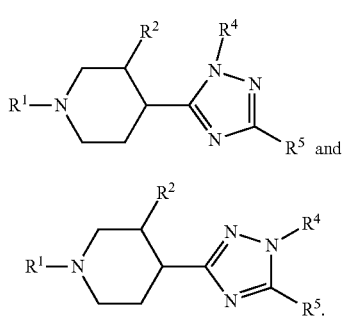

In another embodiment of the present invention, the invention relates to compounds of structural formula Ic-1 and Ic-2:

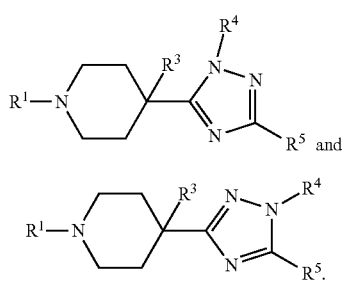

In another embodiment of the present invention, the invention relates to compounds of structural formula Id-1 and Id-2:

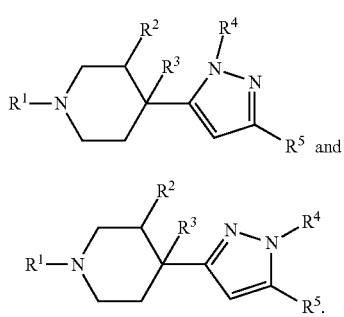

In another embodiment of the present invention, the invention relates to compounds of structural formula Ie-1 and Ie-2:

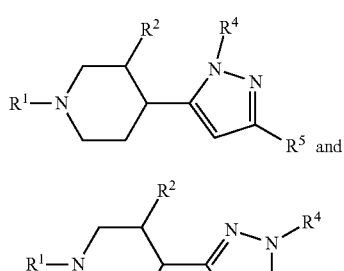

In another embodiment of the present invention, the invention relates to compounds of structural formula If-1 and If-2:

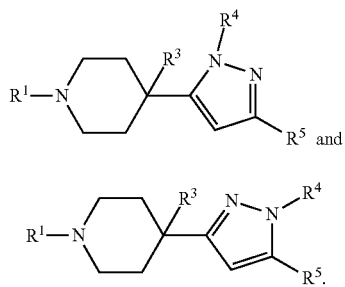

In another embodiment of the present invention, the invention relates to compounds of structural formula Ig-1 and Ig-2:

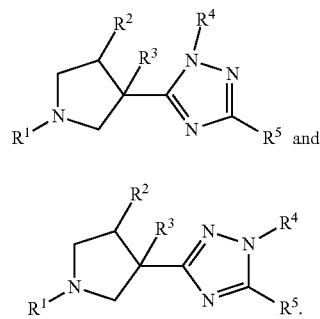

In another embodiment of the present invention, the invention relates to compounds of structural formula Ih-1 and Ih-2:

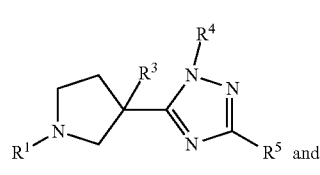

In another embodiment of the present invention, the invention relates to compounds of structural formula Ii-1 and Ii-2:

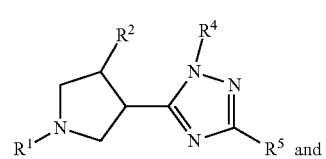

-continued

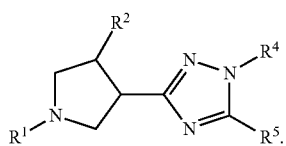
Ii-2

In another embodiment of the present invention, the invention relates to compounds of structural formula Ij-1 and Ij-2:

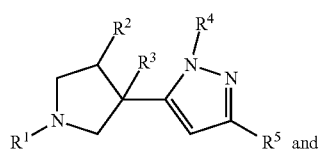
Ij-1 and

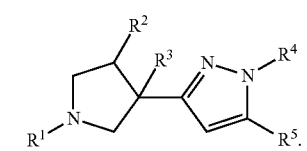
Ij-2

In another embodiment of the present invention, the invention relates to compounds of structural formula Ik-1 and Ik-2:

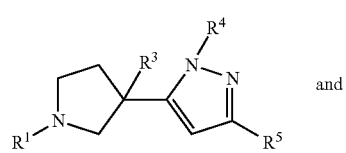
Ik-1 and

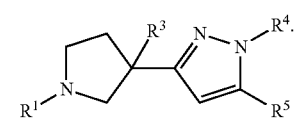
Ik-2

In another embodiment of the present invention, the invention relates to compounds of structural formula Il-1 and Il-2:

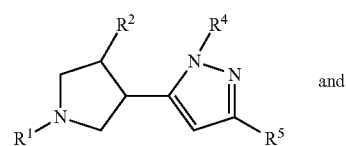
Il-1 and

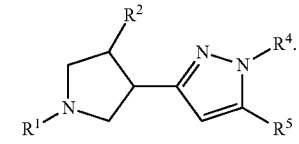
Il-2

Illustrative, but nonlimiting, examples of compounds of the present invention that are useful as inhibitors of PrCP are the following:

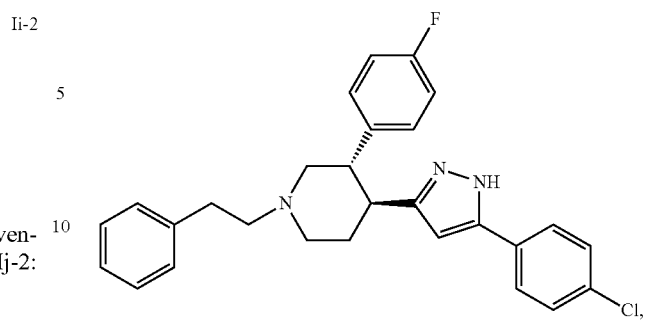

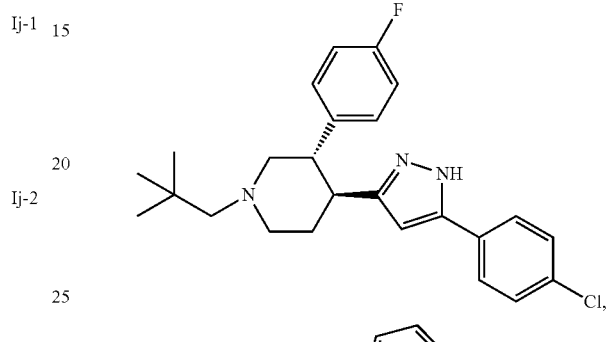

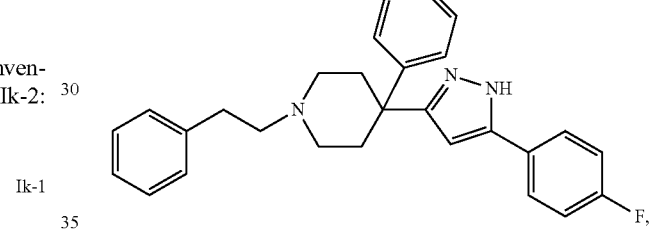

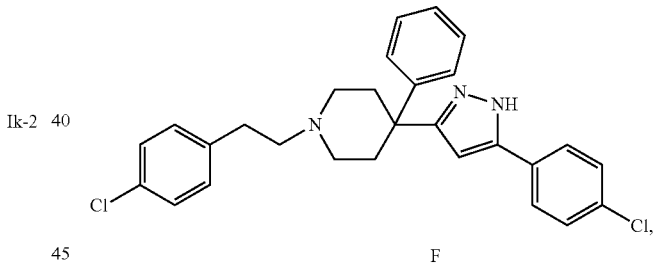

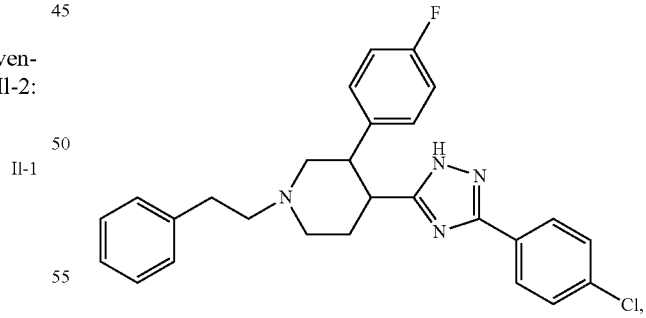

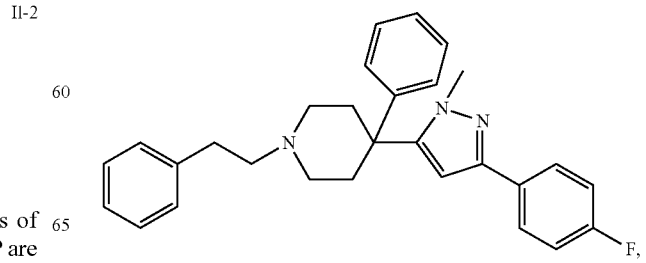

-continued

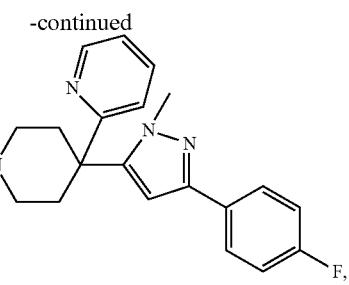

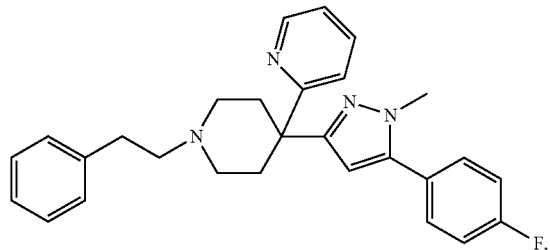

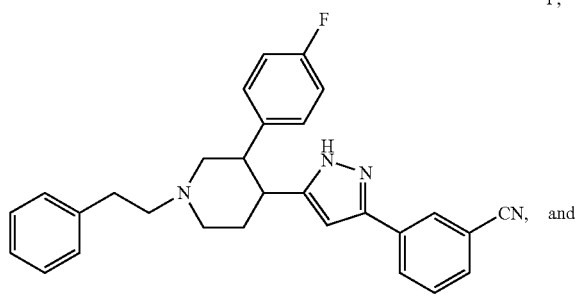

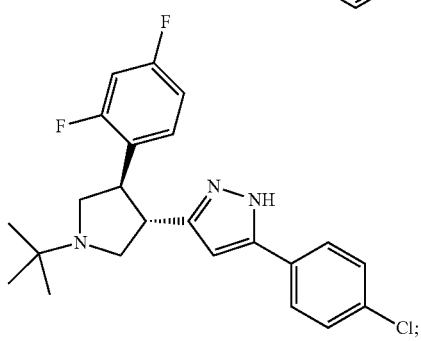

and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. When no number of carbon atoms is specified, $C_{1-6}$ is intended.

"Alkenyl" means carbon chains up to 10 carbons, unless otherwise specified, which contain at least one carbon-carbon double bond, and which may be linear or branched or combinations thereof. Examples of alkenyl include vinyl, allyl, isopropenyl, pentenyl, hexenyl, heptenyl, 1-propenyl, 1-butenyl, 2-butenyl, 2-methyl-2-butenyl, and the like.

"Alkynyl" means carbon chains up to 10 carbons, if not otherwise specified, which contain at least one carbon-carbon triple bond, and which may be linear or branched or combinations thereof. Examples of alkynyl include ethynyl, propynyl, butynyl, pentynyl, 3-methyl-1-pentynyl, 2-heptynyl and the like.

The term "alkoxy" refers to straight or branched chain alkoxides of the number of carbon atoms specified (e.g., $C_{1-6}$ alkoxy), or any number within this range [i.e., methoxy (—OMe), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Cycloalkyl" means mono- or bicyclic or bridged saturated carbocyclic rings, each having from 3 to 14 carbon atoms. Examples of cycloalkyl include cyclopropyl, cyclobutyl, cyclopentyl, cyclohexyl, cycloheptyl, cyclooctyl, and decahydronaphthyl, and the like.

"Cycloalkenyl" means nonaromatic, mono- or bicyclic or bridged carbocyclic rings, each having from 3 to 14 carbon atoms and containing at least one double bond. Examples of cycloalkyl include cyclopropenyl, cyclobutenyl, cyclopentenyl, cyclohexenyl, cycloheptenyl, cyclooxtenyl, decahydronaphthyl, bicyclo[2.2.1]hept-5-en-2-yl, and the like.

"Cycloheteroalkyl" means nonaromatic, mono- or bicyclic or bridged saturated carbocyclic rings, each having from 2 to 14 carbon atoms and containing 1, 2, 3, 4 or 5 heteroatoms selected from N, NH, O and S. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazabicyclo[3.2.1]-octane, and hexahydroindazolyl. The cycloheteroalkyl ring may be substituted on the ring carbons and/or the ring nitrogens.

"Cycloheteroalkenyl" means nonaromatic mono- or bicyclic or bridged rings each having from 2 to 14 carbon atoms containing at least one double bond and containing 1, 2, 3, 4 or 5 heteroatoms selected from N, NH, O and S. Examples of cycloheteroalkenyl include 1,2,4-oxadiazol-5-one, 1,2,4-thiadiazol-5-one, 1,2,4-triazol-3-one, and 1,2,3,6-tetrahydropyridine, dihydro-1,3,4-oxadiazole, and [1,6]-dihydropyridine and the like. In one embodiment of the present invention, cycloheteroalkenyl is dihydro-1,3,4-oxadiazole. In another embodiment of the present invention, cycloheteroalkenyl is [1,6]-dihydropyridine.

"Aryl" means a monocyclic, bicyclic or tricyclic ring system containing 5-14 carbon atoms, wherein at least one of the rings is aromatic. Aryl thus includes ring systems in which an aromatic ring is fused to a non-aromatic ring, such as a cycloalkyl or cycloalkenyl ring. Examples of aryl include phenyl, naphthalene, biphenyl, indane and 5,6,7,8-tetrahydronaphthalene, and the like. In one embodiment of the present invention, aryl is phenyl, naphthalene, biphenyl, indane, and 5,6,7,8-tetrahydronaphthalene. In another embodiment of the present invention, aryl is phenyl, naphthalene, indane and 5,6,7,8-tetrahydronaphthalene. In one class of this embodiment, aryl is phenyl and naphthalene. In another class of this embodiment, aryl is phenyl. In another class of this embodiment, aryl is naphthalene.

"Heteroaryl" means a monocyclic, bicyclic or tricyclic ring system containing 5-14 carbon atoms and containing 1, 2, 3, 4 or 5 heteroatoms selected from N, NH, O and S wherein at least one of the heteroatom containing rings is aromatic. Heteroaryls thus includes heteroaryls fused to other kinds of rings, such as aryls, cycloalkyls and heterocycles that are not aromatic. Heteroaryl includes ring systems in which an aromatic heteroatom containing ring is fused to a non-aromatic ring, such as a cycloalkyl, cycloalkenyl, cycloheteroalkyl or cycloheteroalkenyl ring, and also includes ring systems in which an aryl ring is fused to a non-aromatic heteroatom containing ring, such as a cycloheteroalkyl or cycloheteroalkenyl ring. Examples of heteroaryls include: pyrazole, pyridine, pyrazine, pyrrole, pyrimidine, pyridazine, benzoimidazole, quinoline, isothiazole, isoquinoline, indole, indazole, carbazole, benzotriazole, benzofuran, benzothiazole, benzothiophene, benzoisooxazole, oxazole, oxadiazole, furan, benzoxazole, isoxazole, indoline, isoindoline, tetrazole, imidazole, oxadiazole (in particular, 1,3,4-oxadiazol-2-yl and 1,2,4-oxadiazol-3-yl), thiazole, thiophene, thiadiazole, triazole, triazine, tetrazole, thiene, benzothiazole, bernzopyrazole, benzothiadiazole, dihydrobenzofuran, indazole, isoindole, dihydrobenzothiene, indolizine, cinnoline, phthalazine, quinazoline, naphthyridine, carbazole, quinoxaline, purine, isobenzylfuran, benzothiene, isoquinoline, dibenzofuran, isothiazole, imidazopyridine, benzodioxole, dihydropyridine, dihydropyrrolopyridine, dihydrobenzooxazine, benzodioxole, benzodioxine, pyrrolopyridine, triazolopyridine, dihydropyridooxazine, dihydrobenzoxazine, dihydroindole, dihydroisoindole, dihydrobenzoimidazole, dihydroquinoline, tetrahydroisoquinoline, tetrahydrocyclopentaindole, tetrahydroquinoxaline, and tetrahydropyridine. For heterocycloalkyl and heteroaryl groups, rings and ring systems containing from 3-15 atoms are included, forming 1-3 rings.

"Halogen" includes fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$). In one embodiment of the present invention, halogen is selected from fluorine, chlorine, and bromine.

"Oxo" means the functional group "=O" which is an oxygen atom connected to the molecule via a double bond, such as, for example, (1) "C=(O)", that is a carbonyl group; (2) "S=(O)", that is, a sulfoxide group; and (3) "N=(O)", that is, an N-oxide group, such as pyridyl-N-oxide.

In choosing compounds of the present invention, one of ordinary skill in the art will recognize that the various substituents, i.e. $R^1$, $R^2$, etc., are to be chosen in conformity with well-known principles of chemical structure connectivity and stability. When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the functional group adjacent to the point of attachment is described first, with our without a bond "—", followed by the terminal portion of the designated side chain. For example, a $C_{1-5}$ alkylcarbonylamino $C_{1-6}$alkyl substituent is equivalent to:

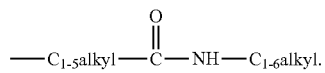

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The terms "compounds of structural formula I" and "formula I" include the compounds of structural formulas I-1, I-2, Ia-1, Ia-2, Ib-1, Ib-2, Ic-1, Ic-2, Id-1, Id-2, Ie-1, Ie-2, If-1, If-2, Ig-1, Ig-2, Ih-1, Ih-2, Ii-1, Ii-2, Ij-1, Ij-2, Ik-1, Ik-2, Il-1, and Il-2, and pharmaceutically acceptable salts thereof. The terms "compounds of structural formula I-1 and/or I-2," and "formula I-1 and/or I-2" include the compounds of structural formulas Ia-1, Ia-2, Ib-1, Ib-2, Ic-1, Ic-2, Id-1, Id-2, Ie-1, Ie-2, If-1, If-2, Ig-1, Ig-2, Ih-1, Ih-2, Ii-1, Ii-2, Ij-1, Ij-2, Ik-1, Ik-2, Il-1, and Il-2, and pharmaceutically acceptable salts thereof.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer of a compound of the general structural formula I may be obtained by stereospecific synthesis using optically pure starting materials or reagents of known absolute configuration.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column. Alternatively, any enantiomer of a compound of the general Formula I may be obtained by stereospecific synthesis using optically pure starting materials or reagents of known configuration.

If desired, racemic mixtures of the compounds may be separated so that the individual enantiomers are isolated. Racemic mixtures can be separated into their individual enantiomers by any of a number of conventional methods, which include chiral chromatography, derivatization with a chiral auxiliary followed by separation by chromatography or crystallization, and fractional crystallization of diastereomeric salts. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts.

For example, a ketone and its enol form are keto-enol tautomers. The individual tautomers as well as mixtures thereof are encompassed with compounds of the present invention.

In the compounds of structural formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations. The compounds of the present invention may be administered in the form of a pharmaceutically acceptable salt.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The compounds of formula I are effective as inhibitors of prolylcarboxypeptidase (PRCP). The compounds of formula I are therefore useful for the treatment, control and/or prevention of diseases, disorders or conditions responsive to the inhibition of the prolylcarboxypeptidase (PRCP) enzyme, including but not limited to: abnormal metabolism, obesity, diabetes, metabolic syndrome, obesity related disorders, diabetes related disorders, hypertension, dyslipidemia, stroke, gallbladder disease, cardiovascular disease, osteoarthritis, rheumatoid arthritis, hypercholesterolemia, stable angina, unstable angina, artherosclerosis, sleep apnea, respiratory problems, cancer, and stroke.

One aspect of the present invention provides a method for the treatment or prevention of disorders, diseases or conditions responsive to the inhibition of prolylcarboxypeptidase in a subject in need thereof which comprises administering to the subject a therapeutically or prophylactically effective amount of a compound of formula I, or a pharmaceutically acceptable salt thereof.

Another aspect of the present invention provides a method for the treatment or prevention of obesity, diabetes, an obesity related disorder or a diabetes related disorder in a subject in need thereof which comprises administering to said subject a therapeutically or prophylactically effective amount of a prolylcarboxypeptidase inhibitor of formula I. Another aspect of the present invention provides a method for the treatment or prevention of obesity in a subject in need thereof which comprises administering to the subject a therapeutically or prophylactically effective amount of a compound of formula I, or a pharmaceutically acceptable salt thereof. Another aspect of the present invention provides a method for reducing food intake in a subject in need thereof which comprises administering to the subject a therapeutically or prophylactically effective amount of a compound of formula I, or a pharmaceutically acceptable salt thereof. Another aspect of the present invention provides a method for reducing body fat mass in a subject in need thereof which comprises administering to the subject a therapeutically or prophylactically effective amount of a compound of formula I, or a pharmaceutically acceptable salt thereof. Another aspect of the present invention provides a method for losing weight in a subject in need thereof which comprises administering to the subject a therapeutically or prophylactically effective amount of a compound of formula I, or a pharmaceutically acceptable salt thereof.

Another aspect of the present invention provides a method for the treatment or prevention of an obesity-related disorder selected from the group consisting of: overeating, binge eating, hypertension, elevated plasma insulin concentrations, insulin resistance, hyperlipidemia, endometrial cancer, breast cancer, prostate cancer, colon cancer, kidney cancer, osteoarthritis, obstructive sleep apnea, heart disease, abnormal heart rhythms and arrythmias, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastro-esophageal reflux, Pickwickian syndrome, inflammation, systemic inflammation of the vasculature, arteriosclerosis, hypercholesterolemia, hyperuricaemia, lower back pain, gallbladder disease, gout, constipation, irritable bowel syndrome, inflammatory bowel syndrome, cardiac hypertrophy, left ventricular hypertrophy, in a subject in need thereof which comprises administering to the subject a therapeutically or prophylactically effective amount of a compound of formula I, or a pharmaceutically acceptable salt thereof.

Another aspect of the present invention provides a method for the treatment or prevention of diabetes, in a subject in need thereof which comprises administering to the subject a therapeutically or prophylactically effective amount of a compound of formula I, or a pharmaceutically acceptable salt thereof.

Another aspect of the present invention provides a method for the treatment or prevention of a diabetes related disorder in a subject in need thereof which comprises administering to the subject a therapeutically or prophylactically effective amount of a compound of formula I, or a pharmaceutically acceptable salt thereof.

Another aspect of the present invention provides a method for the treatment or prevention of a diabetes related disorder selected from the group consisting of: hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, neuropathy, Syndrome X, and ovarian hyperandrogenism (polycystic ovarian syndrome), in a subject in need thereof which comprises administering to the subject a therapeutically or prophylactically effective amount of a compound of formula I, or a pharmaceutically acceptable salt thereof.

The present invention also relates to methods for treating or preventing obesity by administering a compound of formula I in combination with a therapeutically or prophylactically effective amount of another agent known to be useful to treat or prevent the condition. The present invention also relates to methods for treating or preventing diabetes by administering a compound of formula I in combination with a therapeutically or prophylactically effective amount of another agent known to be useful to treat or prevent the condition. The present invention also relates to methods for treating or preventing obesity related disorders by administering a compound of formula I in combination with a therapeutically or prophylactically effective amount of another agent known to be useful to treat or prevent the condition. Yet another aspect of the present invention relates to the use of a therapeutically effective amount of a compound of formula I, or a pharmaceutically acceptable salt or ester thereof, and a therapeutically effective amount of at least one agent selected from the group consisting of: simvastatin, mevastatin, ezetimibe, atorvastatin, sitagliptin, metformin, sibutramine, orlistat, Qnexa, topiramate, phentermine, losartan, losartan with hydrochlorothiazide, or rimonabant, or a pharmaceutically acceptable salt or ester or prodrug thereof, for the manufacture of a medicament useful for the treatment, control, or prevention of obesity, diabetes, a diabetes related disorder, or an obesity-related disorder in a subject in need of such treatment.

Another aspect of the present invention provides a pharmaceutical composition comprising a compound of formula I, and a pharmaceutically acceptable carrier.

Yet another aspect of the present invention relates to the use of a compound of formula I for the manufacture of a medicament useful for the treatment or prevention, or suppression of a disease mediated by prolylcarboxypeptidase (PRCP) in a subject in need thereof.

Yet another aspect of the present invention relates to the use of a compound of formula I for the manufacture of a medicament useful for the treatment or prevention, or suppression of a disease mediated by prolylcarboxypeptidase (PRCP), wherein the disease is selected from the group consisting of obesity, diabetes, an obesity-related disorder and a diabetes related disorder in a subject in need thereof.

Yet another aspect of the present invention relates to the use of a therapeutically effective amount of a compound of formula I, or a pharmaceutically acceptable salt thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4) inhibitor, a glucagons like peptide 1 (GLP-1) agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid CB 1 receptor antagonist or inverse agonist, a melanin-concentrating hormone receptor antagonist, a melanocortin 4 receptor agonist, a bombesin receptor subtype δ agonist, a ghrelin receptor antagonist, PYY, $PYY_{3-36}$, and a NK-1 antagonist, or a pharmaceutically acceptable salt thereof, for the manufacture of a medicament useful for the treatment, control, or prevention of obesity, diabetes or an obesity-related disorder in a subject in need of such treatment. Yet another aspect of the present invention relates to the use of a therapeutically effective amount of a compound of formula I, and pharmaceutically acceptable salts and esters thereof, and a therapeutically effective amount of an agent selected from the group consisting of an insulin sensitizer, an insulin mimetic, a sulfonylurea, an α-glucosidase inhibitor, a dipeptydyl peptidase 4 inhibitor, a glucagon-like peptide 1 agonist, a HMG-CoA reductase inhibitor, a serotonergic agent, a pa-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype δ agonist, a ghrelin receptor antagonist, PYY, $PYY_{3-36}$, and a NK-1 antagonist, or a pharmaceutically acceptable salt thereof, for the manufacture of a medicament for treatment or prevention of obesity, diabetes, an obesity related disorder or a diabetes related disorder which comprises an effective amount of a the compound of formula I, and an effective amount of the agent, together or separately. Yet another aspect of the present invention relates to a product containing a therapeutically effective amount of a compound of formula I, or a pharmaceutically acceptable salt thereof; and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanocortin 4 receptor agonist, a melanin-concentrating hormone receptor antagonist, a bombesin receptor subtype δ agonist, a ghrelin receptor antagonist, PYY, $PYY_{3-36}$, and a NK-1 antagonist, or a pharmaceutically acceptable salt thereof, as a combined preparation for simultaneous, separate or sequential use in obesity, diabetes, an obesity-related disorder or a diabetes related disorder.

The compounds of formula I can be provided in kit. Such a kit typically contains an active compound in dosage forms for administration. A dosage form contains a sufficient amount of active compound such that a beneficial effect can be obtained when administered to a patient during regular intervals, such as 1, 2, 3, 4, 5 or 6 times a day, during the course of I or more days. Preferably, a kit contains instructions indicating the use of the dosage form for weight reduction (e.g., to treat obesity) and the amount of dosage form to be taken over a specified time period.

Compounds of formula I are inhibitors of prolylcarboxypeptidase (PRCP) and as such are useful in the treatment, control or prevention of diseases, disorders or conditions responsive to the modulation of prolylcarboxypeptidase (PRCP). Such diseases, disorders or conditions include, but are not limited to, abnormal metabolism, obesity, diabetes, metabolic syndrome, obesity related disorders, diabetes related disorders, hypertension, dyslipidemia, stroke, gallbladder disease, cardiovascular disease, osteoarthritis, rheumatoid arthritis, hypercholesterolemia, stable angina, unstable angina, artherosclerosis, sleep apnea, respiratory problems, cancer, and stroke. Such diseases, conditions and disorders also include non-obese overweight conditions and normal weight conditions where weight control or management is desired in order to prevent an obese or overweight condition from developing, or to maintain a healthy weight.

The compounds of formula I, and compositions thereof, are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating, binge eating, bulimia nervosa, hypertension, type 2 diabetes, elevated plasma insulin concentrations, hyperinsulinemia, insulin resistance, glucose intolerance, dyslipidemia, hyperlipidemia, endometrial cancer, breast cancer, prostate cancer, kidney cancer, colon cancer, osteoarthritis, obstructive sleep apnea, cholelithiasis, cholecystitis, gallstones, gout, gallbladder disease, abnormal heart rhythms and arrythmias, myocardial infarction, congestive heart failure, coronary heart disease, angina pectoris, sudden death, stroke, metabolic syndrome, psychological disorders (depression, eating disorders, distorted body-weight, and low self esteem), and other pathological conditions showing reduced metabolic activity or a decrease in resting energy expenditure as a percentage of total fat-free mass, e.g., children with acute lymphoblastic leukemia. Further examples of obesity-related disorders are sexual and reproductive dysfunction, such as polycystic ovary disease, infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. Additionally, the present compounds are useful in the treatment of any condition in which it is desirable to lose weight or to reduce food intake. Additionally, the present compounds are useful in the treatment of any condition in which it is desirable to enhance cognition and memory, such as Alzheimer's Disease. The compositions of the present invention are also useful for reducing the risk of secondary outcomes of obesity, such as reducing the risk of left ventricular hypertrophy. Therefore, the present invention provides methods of treatment or prevention of such diseases, conditions and/or disorders modulated by prolylcarboxypeptidase (PRCP) in an animal which comprises administering to the animal in need of such treatment a compound of formula I, in particular a therapeutically or prophylactically effective amount thereof.

The term "inhibitor" as used herein means a composition of matter which when administered to a mammal, such as a human, inhibits the biological activity attributable to the level or presence of an endogenous compound in the mammal. Inhibition of PrCP includes, but is not limited to, inhibiting the biological activity of the PrCP enzyme or molecule.

The term "subject" means a mammal. One embodiment of the term "mammal" is a "human," said human being either male or female. The instant compounds are also useful for treating or preventing obesity and obesity related disorders in cats and dogs. As such, the term "mammal" includes companion animals such as cats and dogs. The term "mammal in need thereof" refers to a mammal who is in need of treatment or prophylaxis as determined by a researcher, veterinarian, medical doctor or other clinician.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Diabetes is characterized by a fasting plasma glucose level of greater than or equal to 126 mg/dl. A diabetic subject has a fasting plasma glucose level of greater than or equal to 126 mg/dl. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

"Diabetes related disorders" are diseases, disorders and conditions that are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, inhibitors of prolylcarboxypeptidase (PRCP) may also be useful to treat hypertension associated with this condition.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of the treatment of diabetes is to reduce an increased plasma glucose concentration. Another outcome of the treatment of diabetes is to reduce an increased insulin concentration. Still another outcome of the treatment of diabetes is to reduce an increased blood triglyceride concentration. Still another outcome of the treatment of diabetes is to increase insulin sensitivity. Still another outcome of the treatment of diabetes may be enhancing glucose tolerance in a subject with glucose intolerance. Still another outcome of the treatment of diabetes is to reduce insulin resistance. Another outcome of the treatment of diabetes is to lower plasma insulin levels. Still another outcome of treatment of diabetes is an improvement in glycemic control, particularly in type 2 diabetes.

Prevention of diabetes mellitus, in particular diabetes associated with obesity, refers to the administration of a compound or combination of the present invention to prevent or treat the onset of diabetes in a subject in need thereof. A subject in need of preventing diabetes in a pre-diabetic subject.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$.

An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus-type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, hypertension, dyslipidemia, insulin resistance, hypercholesterolemia, hypertriglyceridemia, and cholelithiasis.

The terms "administration of" and or "administering" a compound should be understood to mean providing a compound of the invention or a prodrug of a compound of the invention to a subject in need of treatment. The administration of the compounds of the present invention in order to practice the present methods of therapy is carried out by administering a therapeutically effective amount of the compound to a subject in need of such treatment or prophylaxis. The need for a prophylactic administration according to the methods of the present invention is determined via the use of well known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art. The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder. The therapeutically or prophylactically effective amount, or dosage, of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgement.

Administration and Dose Ranges

Any suitable route of administration may be employed for providing a subject or mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

The effective dosage of active ingredient employed may vary depending on the particular compound employed, the mode of administration, the condition being treated and the severity of the condition being treated. Such dosage may be ascertained readily by a person skilled in the art.

Generally satisfactory results are obtained when the compounds of formula I are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

In the case where an oral composition is employed, a suitable dosage range is, e.g. from about 0.01 mg to about 1500 mg of a compound of Formula I per day, preferably from about 0.1 mg to about 600 mg per day, more preferably from about 0.1 mg to about 100 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 600, 750, 1000, 1250 or 1500 milligrams of the active ingredient for the symptomatic adjustment of the dosage to the patient to be treated.

For use where a composition for intranasal administration is employed, intranasal formulations for intranasal administration comprising 0.001-10% by weight solutions or suspensions of the compounds of formula I in an acceptable intranasal formulation may be used.

For use where a composition for intravenous administration is employed, a suitable dosage range is from about 0.001 mg to about 50 mg, preferably from 0.01 mg to about 50 mg, more preferably 0.1 mg to 10 mg, of a compound of formula I per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001-1% by weight solutions or suspensions of the compounds of formula I in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual patient. Such dosage may be ascertained readily by a person skilled in the art.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPAR agonists, when the patient's glycemic levels are not adequately responding to treatment.

When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, LY-818, and compounds disclosed in WO02/08188, WO2004/020408, and WO2004/020409.

(b) biguanides, such as metformin and phenformin;

(c) protein tyrosine phosphatase-1B (PTP-1B) inhibitors;

(d) dipeptidyl peptidase-IV (DPP-4) inhibitors, such as sitagliptin, saxagliptin, vildagliptin, and alogliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPARαc agonists, such as feriofibric acid derivatives (gemfibrozil, clofibrate, fenofibrate and bezafibrate), (v) cholesterol absorption inhibitors, such as ezetimibe, (vi) acyl CoA:cholesterol acyltransferase (ACAT) inhibitors, such as avasimibe, (vii) CETP inhibitors, such as torcetrapib, and (viii) phenolic antioxidants, such as probucol;

(i) PPARα/γ dual agonists, such as muraglitazar, tesaglitazar, farglitazar, and JT-501;

(j) PPARδ agonists, such as those disclosed in WO97/28149;

(k) anti-obesity compounds, such as fenfluramine, dexfenfluramine, phentiramine, subitramine, orlistat, neuropeptide Y Y5 inhibitors, MC4R agonists, cannabinoid receptor 1 (CB-1) antagonists/inverse agonists (e.g., rimonabant and taranabant), and β$_3$ adrenergic receptor agonists;

(l) ileal bile acid transporter inhibitors;

(m) agents intended for use in inflammatory conditions, such as aspirin, non-steroidal anti-inflammatory drugs, glucocorticoids, azulfidine, and cyclooxygenase-2 (Cox-2) selective inhibitors;

(n) glucagon receptor antagonists;

(O) GLP-1;

(p) GIP-1;

(q) GLP-1 analogs and derivatives, such as exendins, (e.g., exenatide and liruglatide);

(r) 11β-hydroxysteroid dehydrogenase-1 (HSD-1) inhibitors;

(s) inhibitors of cholesteryl ester transfer protein (CETP), such as torcetrapib;

(t) SSTR3 antagonists;

(u) other SSTR5 antagonists;

(v) acetyl CoA carboxylase-1 and/or -2 inhibitors;

(w) AMPK activators;

(x) agonists of GPR-119;

(y) glucokinase agonists; and (z) FGF-21 agonists.

The above combinations include combinations of a compound of the present invention not only with one other active compound, but also with two or more other active compounds. Non-limiting examples include combinations of compounds having Formula T with two or more active compounds selected from biguanides, sulfonylureas, HMG-CoA reductase inhibitors, other PPAR agonists, PTP-113 inhibitors, DPP-4 inhibitors, and cannabinoid receptor 1 (CB1) inverse agonists/antagonists.

Antiobesity compounds that can be combined with compounds described herein include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of anti-obesity compounds that can be combined with compounds described herein, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds described herein include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds described herein include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292,736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Suitable melanocortin-4 receptor (MC4R) agonists include, but are not limited to, those disclosed in U.S. Pat. No. 6,294,534, U.S. Pat. Nos. 6,350,760, 6,376,509, 6,410,548, 6,458,790, U.S. Pat. No. 6,472,398, U.S. Pat. No. 5,837,521, U.S. Pat. No. 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02/092566, WO 03/-093234, WO 03/095474, and WO 03/104761.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide.

Examples of other anti-obesity agents that can be employed in combination with a compound of formula I, II, III or IV are disclosed in "Patent focus on new anti-obesity agents," *Exp. Opin, Ther. Patents,* 10: 819-831 (2000); "Novel anti-obesity drugs," *Exp. Opin. Invest. Drugs,* 9: 1317-1326 (2000); and "Recent advances in feeding suppressing agents: potential therapeutic strategy for the treatment of obesity, *Exp. Opin. Ther. Patents,* 11: 1677-1692 (2001). The role of neuropeptide Y in obesity is discussed in *Exp. Opin. Invest. Drugs,* 9: 1327-1346 (2000), Cannabinoid receptor ligands are discussed in *Exp. Opin. Invest. Drugs,* 9: 1553-1571 (2000).

The instant invention also includes administration of a single pharmaceutical dosage formulation which contains both a compound of formula I in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly. Administration in these various ways are suitable for the present compositions as long as the beneficial pharmaceutical effect of the combination of the compound of formula I and the second active ingredient is realized by the patient at substantially the same time. Such beneficial effect is preferably achieved when the target blood level concentrations of each active ingredient are maintained at substantially the same time. It is preferred that the combination of the compound of formula I and the second active ingredient be co-administered concurrently on a once-a-day dosing schedule; however, varying dosing schedules, such as the compound of formula I once a day and the second active ingredient once, twice or more times per day or the compound of formula I three times a day and the second active ingredient once, twice or more times per day, is also encompassed herein. A single oral dosage formulation comprised of both a compound of formula I and a second active ingredient is preferred. A single dosage formulation will provide convenience for the patient, which is an important consideration especially for patients with diabetes or obese patients who may be in need of multiple medications.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the compound of formula I, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form. In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Pharmaceutical Compositions

Another aspect of the present invention provides pharmaceutical compositions which comprise a compound of formula I, as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the typical oral dosage unit form, in which case solid pharmaceutical carriers are typically employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of formula I of the present invention can be prepared according to the procedures of the following Schemes and Examples, using appropriate materials and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. All temperatures are degrees Celsius unless otherwise noted. Mass spectra (MS) were measured by electrospray ion-mass spectroscopy (ESMS).

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T. and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

General Methods

Reactions sensitive to moisture or air were performed under nitrogen using anhydrous solvents and reagents. The progress of reactions was determined by either analytical thin layer chromatography (TLC) performed with E. Merck pre-coated TLC plates, silica gel 60E-254, layer thickness 0.25 mm or liquid chromatography-mass spectrum (LC-MS). Analytical HPLC/MS—Standard Method: Mass analysis was performed on a Waters Micromas® ZQ™ with electrospray ionization in positive ion detection mode. For HPLC/MS data, the two HPLC conditions used were as follows: 1) LC-2 (Waters C18 XTerra™ 3.5 µm 2.1×20 mm column with gradient 10:90-98:2 v/v $CH_3CN/H_2O$+v 0.05% TFA over 1.25 min then hold at 98:2 v/v $CH_3CN/H_2O$+v 0.05% TFA for 0.75 min; flow rate 1.5 mL/min, UV wavelength 254 nm); and 2) LC-4 (Waters C18 XTerra 3.5 µm 2.1×20 mm column with gradient 10:90-98:2 v/v $CH_3CN/H_2O$+v 0.05% TFA over 3.25 min then hold at 98:2 v/v $CH_3CN/H_2O$+v 0.05% TFA for 0.75 min; flow rate 1.5 mL/min, UV wavelength 254 nm). Preparative reverse phase high performance liquid chromatography (RP-HPLC) used for the purification of samples was performed using a Gilson™ RP-HPLC system with an Akzo-Nobel Kromasil™ 100-5C18 column (21.2 mm×10 cm), 25 mL/min gradient elution 10:90 to 100:0 $CH_3CN/H_2O$+v 0.05% TFA over 12 min. Concentration of solutions was carried out on a rotary evaporator under reduced pressure. Flash chromatography was performed using a Biotage Isolera™, Horizon™ or SP1 Flash Chromatography apparatus (Dyax Corp.) on silica gel (32-63 µM particle size, KP-Sil 60 Å packing material type) in pre-packed cartridges or using an ISCO CombiFlash™ Sq 16× or CombiFlash® Companion™ apparatus on silica gel (32-63 µM, 60 Å) in pre-packed cartridges. Microwave reactions were carried out on a Biotage Initiator™ 2.0 or CEM Discover™ system.

Abbreviations Used in the Description of the Preparation of the Compounds of the Present Invention:

ACN is acetonitrile; $Ac_2O$ is acetic anhydride; Ac is acetyl; AcOH is acetic acid; aq is aqueous; Boc and BOC is tert-butoxycarbonyl; $BOC_2O$ is di-tert-butyl dicarbonate; Bn is benzyl; BuLi is butyl lithium; brine is saturated aqueous sodium chloride solution; CDI is 1,1'-carbonyldiimidazole; Celite™ is diatomaceous earth; $CO_2$ is carbon dioxide; CO is carbon monoxide; DCM or $CH_2Cl_2$ is dichloromethane; dppf is 1,1''-bis(diphenylphosphino)ferrocene; DBU is 1,8-diazabicyclo[5.4.0]undec-7-ene; DEA is diethylamine; DIPEA and DIEA is N,N-diisopropylethylamine; DMAP is 4-N,N-dimethylaminopyridine; DME is 1,2-dimethoxyethane; DMF is N,N-dimethyl-formamide; DMA is N,N-dimethylacetamide; DMSO is dimethyl sulfoxide; EDC is N-ethyl-N'-(3-dimethylaminopropyl)carbodiimide; EtOAc is ethyl acetate; Et (et) is ethyl; EA and EtOAc is ethyl acetate; equiv is equivalent(s); ESI is electrospray ioinization; $Et_3N$ is triethylamine; $Et_3SiH$ is triethylsilane; EtOH is ethanol; $Et_2O$ or ether is diethyl ether; g is grams; h or hr is hour(s); HATU is O-(7-azabenzotriazol-1-yl)-N,N,N',N'-tetramethyluronium hexafluorophosphate; HBTU is N,N,N',N'-tetramethyl-O-(1H-benzotriazol-1-yl)uronium hexafluorophosphate; HCl is hydrochloric acid; HOAt is 3H-[1,2,3]-triazolo[4,5-b]pyridin-3-ol; HOBT or HOBt is 1-hydroxybenzotriazole; HPLC is high-performance liquid chromatography; in vacuo is rotary evaporation under reduced pressure; i-Pr is isopropyl; i-Pr is isopropyl; i-PrOH or IPA is isopropyl alcohol; LC is liquid chromatography; LC/MS is liquid chromatography/mass spectroscopy; L is liter(s); m-CPBA is 3-chloroperbenzoic acid; mg is milligrams; ml and mL is milliliter; M is molar; mmol is millimole(s); Me is methyl; MeCN or ACN is acetonitrile; MeOH is methanol; min is minute(s); ms or MS is mass spectrum; MTBE is methyl-tert-butyl ether; μg is microgram(s); μL is microliter(s); N is normal; NaOEt is sodium ethoxide; NaOMe is sodium methoxide; NaOAc is sodium acetate; NMR is nuclear magnetic resonance spectroscopy; NOE is nuclear Overhauser effect; PE is petroleum ether; Ph is phenyl; RP or rp is reverse phase; HPLC is high-performance liquid chromatography; RP-HPLC is reverse phase high-performance liquid chromatography; $R_f$ is retention time; RT, r.t. and rt is room temperature; sat., sat'd., and sat is saturated; SF is supercritical fluid; SFC is supercritical fluid chromatography; SFC conditions are supercritical $CO_2$ eluant modified with acetonitrile and/or methanol and/or additional modifiers such as diethylamine using the stated column packing material; TEA is triethyl amine; TFA is trifluoroacetic acid; TFAA is trifluoroacetic anhydride; THF is tetrahydrofuran; TLC is thin layer chromatography; TMS is trimethylsilyl or tetramethylsilane; OTMS is trimethylsilyloxy; TsOH is para-toluene sulfonic acid; v is volume; v/v is volume per volume (ratio); and wt % is weight percent.

The compounds of this invention may be prepared in the manner depicted in the following schemes using methods known in the literature and by the methods outlined in the experimental procedures. The procedures given within this invention are for illustration of how an individual skilled in the art of organic synthesis may prepare the exemplary compounds, and therefore are not limited to the examples shown or to the particular substituents shown.

Several strategies may be employed for accessing the compounds described in this invention. Scheme 1 depicts a route for accessing compounds of the general structures 1-7 and 1-8 wherein $R^3$ is not hydrogen. Coupling of a suitable carboxylic acid such as 1-1 with N,O-dimethylhydroxylamine using EDC and HOAt in DMF affords the corresponding Weinreb amide 1-2. Addition of methyl magnesium bromide to Weinreb amide 1-2 in THF affords the methyl ketone 1-3. Claisen-type condensation of the methyl ketone 1-3 and an ester under basic conditions such as sodium hydride in THF affords the 1,3-dicarbonyl 1-4, which is then condensed with a hydrazine in methanol to afford a mixture of pyrazoles 1-5 and 1-6. The pyrazoles may be separated or carried forward as a mixture of regiosiomers. Acidic conditions such as HCl in methanol are used to remove the BOC group from 1-5 and 1-6 to afford the secondary amine, which is further reacted with an electrophile such as an alkyl bromide to afford the tertiary amines 1-7 and 1-8.

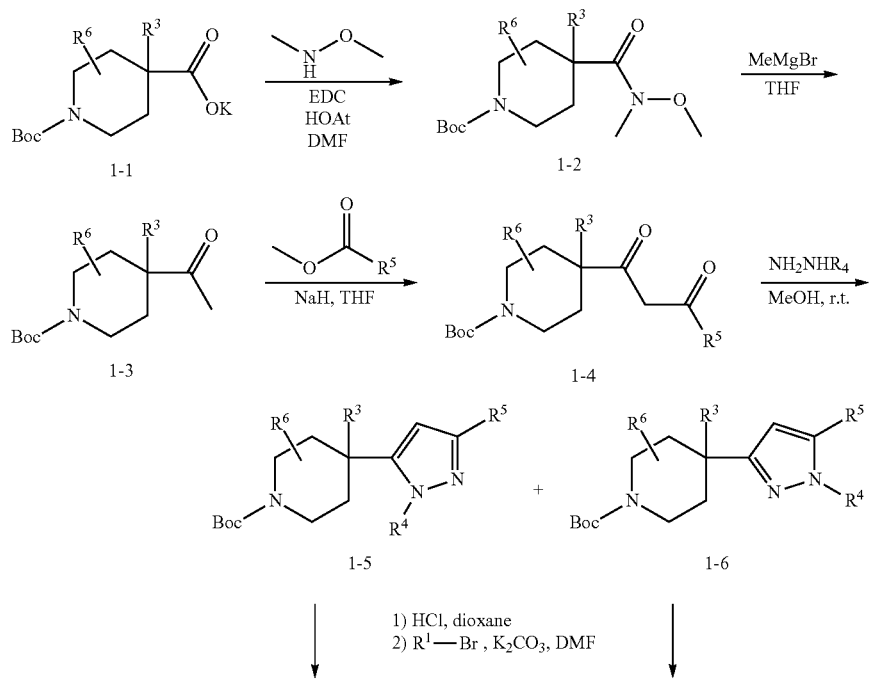

Scheme 1

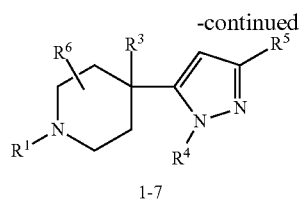
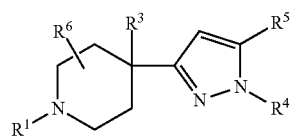

1-7

1-8

Scheme 2 depicts a method for the preparation of compounds of the general structure 2-4 and 2-5, where $R^2$ is not hydrogen. A suitably functionalized carboxylic acid of the general structure 2-1 is activated with CDI in THF to afford an acyl imidazole which is added to a solution of a methyl ketone and sodium hydride to afford a 1,3-diketo intermediate. The di-keto intermediate is then condensed with a hydrazine to afford the pyrazole ring system. Removal of the BOC from the nitrogen under acidic conditions affords intermediates 2-2 and 2-3, which are either separated to afford each individual regioisomer or carried forward as a mixture of regioisomers. Intermediates 2-2 and 2-3 are further reacted with a suitable electrophile to afford the corresponding tertiary amines, which are depicted by structures 2-4 and 2-5.

Scheme 3 depicts an alternate method to that shown in Scheme 2 for the synthesis of compounds where $R^2$ is not hydrogen. A suitably functionalized carboxylic acid such as 3-1 is activated with CDT in THF to afford an intermediate acyl imidazole. This intermediate is added to a solution of a methyl ketone and sodium hydride to afford a 1,3-diketone intermediate, which is condensed with a hydrazine to afford compounds of the general structures 3-2 and 3-3.

Scheme 3

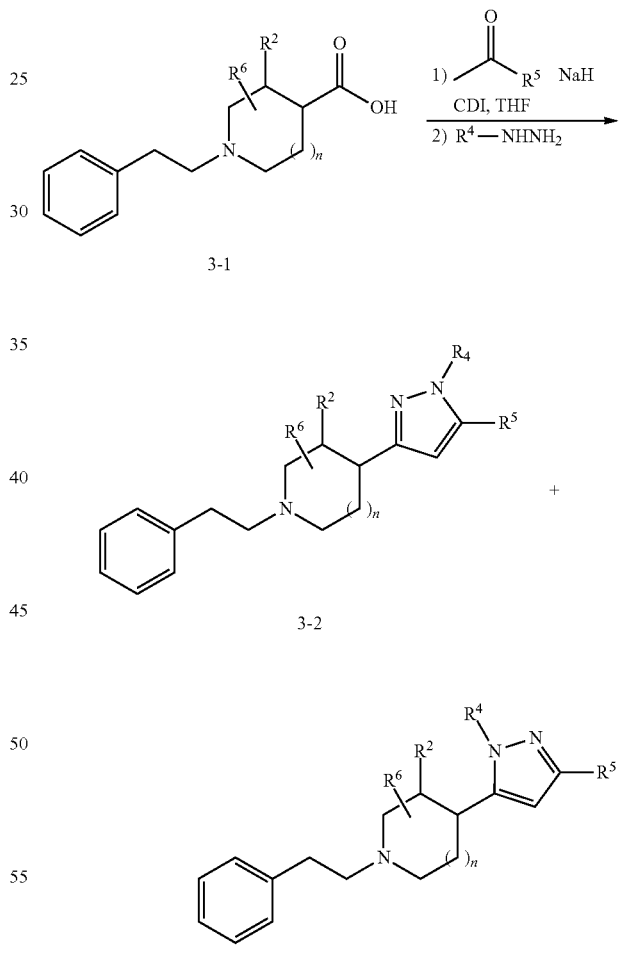

$n = 0, 1$

Scheme 2

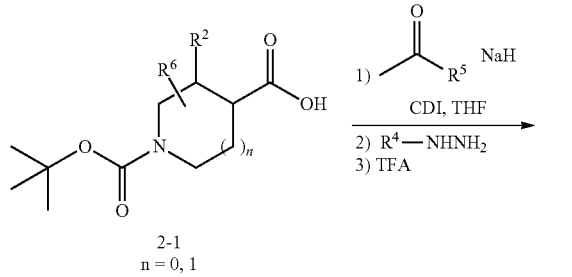

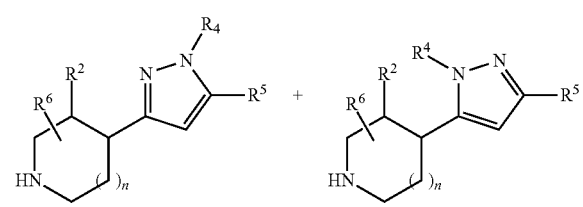

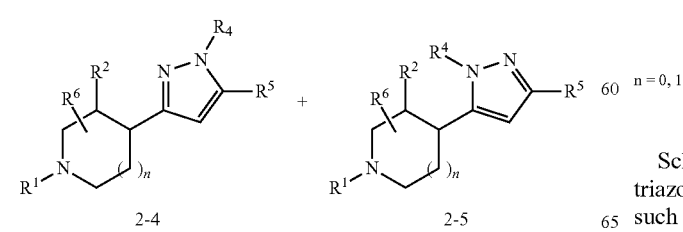

Scheme 4 depicts a general method for the synthesis of the triazole analogs. A suitably functionalized carboxylic acid such as 4-1 is reacted with HBTU and a suitable thioamide, followed by condensation with a hydrazine at an elevated temperature to afford the traiazole 4-2.

Scheme 4

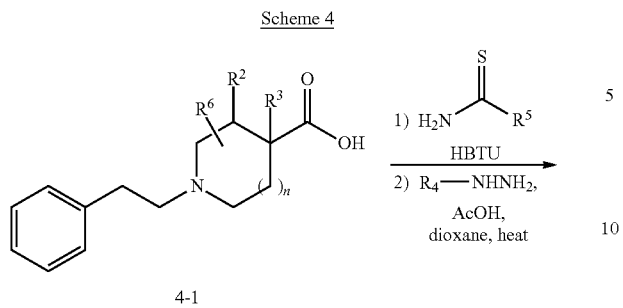

4-1

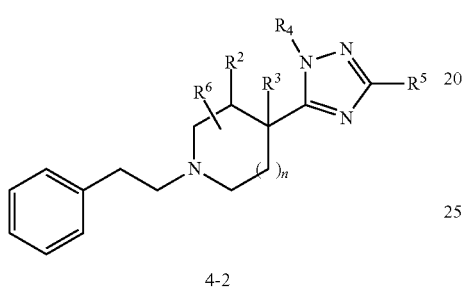

4-2

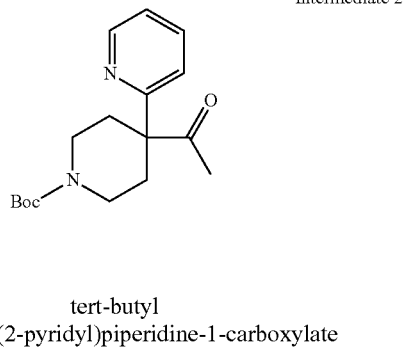

Intermediate 2 tert-butyl 4-acetyl-4-(2-pyridyl)piperidine-1-carboxylate

Methylmagnesium bromide in ether (3.0 M, 3.5 ml, 10.5 mmol) was diluted with THF (5 ml) at −50° C. and treated with a solution of Intermediate 1 (0.9 g, 3.0 mmol) in THF (15 ml). After stirring at −50° C. for 1 hr, the cooling bath was removed and the mixture was warmed up to r.t. and stirred for approximately 16 h. The mixture was then diluted with EtOAc, poured into water and the organic layer was separated. The aqueous layer was extracted with EtOAc and the combined organic layers were dried with anhydrous sodium sulfate, filtered and the filtrate was concentrated. The resulting crude product was purified on silica gel column (0 to 50% EtOAc/hexanes) to give the tile compound. HPLC/MS: 205.3 (M+1), $R_t$=1.13 min (LC-4 HPLC conditions).

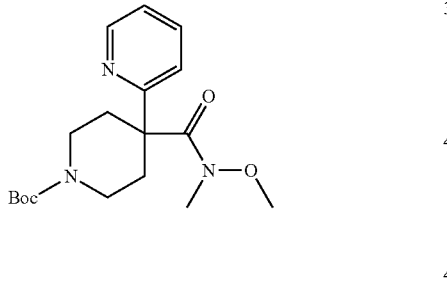

Intermediate 1 tert-butyl 4-(methoxy(methyl)carbamoyl)-4-(2-pyridyl)piperidine-1-carboxylate

To a mixture of 1-tert-butoxycarbonyl-4-(2-pyridyppiperidine-4-carboxylate potassium salt (1.84 g, 5.34 mmol, prepared according to the procedure disclosed in WO 9426735), N,O-dimethylhydroxylamine hydrochloride (0.80 g, 8.0 mmol) and 1-hydroxy-7-azabenzotriazole (0.6 M in DMF, 1.8 ml, 1.1 mmol) in DMF (20 ml) was added diisopropylethylamine (2.7 g, 20.9 mmol) and EDC (2.0 g, 12.9 mmol). After stirring at room temperature overnight, the reaction mixture was treated with saturated ammonium chloride solution and extracted with EtOAc. The combined organic portions were washed with water and brine, then dried over anhydrous sodium sulfate, and filtered. The filtrate was concentrated to give the crude product. Purification of the crude product by column chromatography on silica gel (0 to 10% MeOH/CH$_2$Cl$_2$) afforded the title compound. HPLC/MS: 350.2 (M+1), $R_t$=1.14 min (LC-4 HPLC conditions).

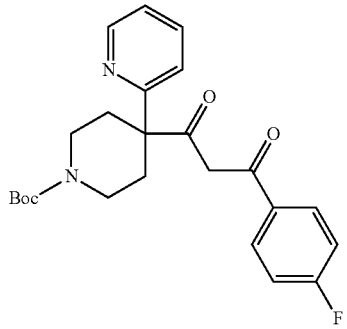

Intermediate 3 tert-butyl 4-[3-(4-fluorophenyl)-3-oxo-propanoyl]-4-(2-pyridyl)piperidine-1-carboxylate Intermediate 2 (411 mg, 1.35 mmol) in THF (10 mL) was treated with methyl 4-fluorobenzoate (276 mg, 1.76 mmol) and sodium hydride (81 mg, 2.0 mmol) at rt. The mixture was heated at reflux overnight, then cooled to 0° C., treated with EtOAc and the pH was adjusted to pH-5 with 1 N HCl (1 ml). The resulting mixture was poured into water and extracted with ethyl acetate. The combined organics were dried with anhydrous Na$_2$SO$_4$, then filtered, and the filtrate was concentrated. The resulting crude product was purified by chromatography on silica gel (0 to 50% EtOAc/hexanes) to give the title compound. HPLC/MS: 449.3 (M+1), $R_t$=1.29 min (LC-4 HPLC conditions).

Intermediates 4 and 5

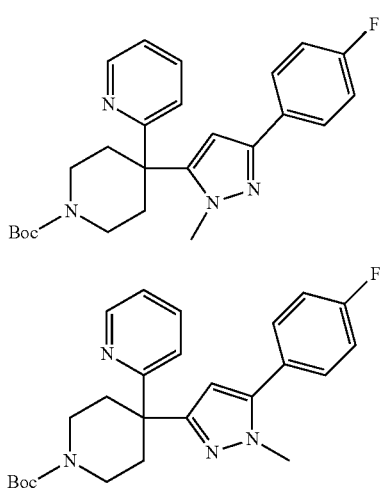

Intermediate 4

Intermediate 5 tert-butyl 4-[5-(4-fluorophenyl)-2-methyl-pyrazol-3-yl]-4-(2-pyridyl)piperidine-1-carboxylate and tert-butyl 4-[5-(4-fluorophenyl)-1-methyl-pyrazol-3-yl]-4-(2-pyridyl)piperidine-1-carboxylate To the solution of Intermediate 3 (161 mg, 0378 mmol) in methanol (2.5 ml) was added a solution of methylhydrazine in methanol (0.5 ml). After stirring at r.t. overnight, the solvent was removed under reduced pressure. The resulting residue was purified by chromatography on silica gel (0-10% methanol/methylene chloride) to give the two separate isomeric pyrazoles: tert-butyl 4-[5-(4-fluorophenyl)-2-methyl-pyrazol-3-yl]-4-(2-pyridyl)piperidine-1-carboxylate (Intermediates 4): HPLC/MS: 381.2 (M-55), $R_t$=1.22 min (LC-4 HPLC conditions); and tert-butyl 4-[5-(4-fluorophenyl)-1-methyl-pyrazol-3-yl]-4-(2-pyridyl)piperidine-1-carboxylate (Intermediate 5): HPLC/MS: 381.2 (M-55), $R_t$=1.16 min. The regiochemistry was assigned by $^1$H NMR and NOE difference experiments.

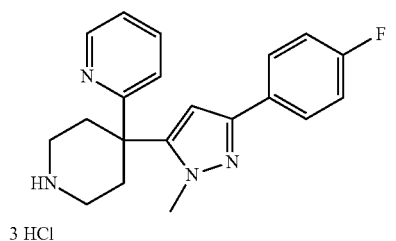

Intermediate 6

3 HCl

2-[4-[5-(4-fluorophenyl)-2-methyl-pyrazol-3-yl]-4-piperidyl]pyridine tris(hydrochloride) salt Intermediates 4 (16.8 mg, 0.038) was dissolved in 1,4-dioxane (1 ml) and treated with 4 N HCl solution in 1,4-dioxane (1 ml). After stirring at room temperature for 2 hr, the mixture was concentrated under reduced pressure to afford the title compound. HPLC/MS: 337.1 (M+1), $R_t$=0.98 min.

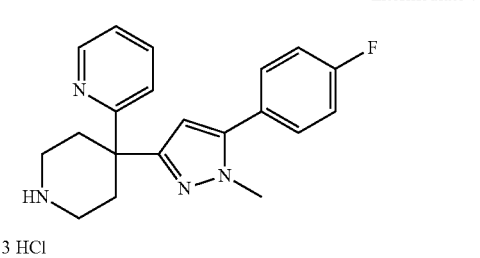

Intermediate 7

3 HCl

2-[4-[5-(4-fluorophenyl)-1-methyl-pyrazol-3-yl]-4-piperidyl]pyridine tris(hydrochloride) salt Intermediate 5 (72.1 mg, 0.165 mmol) was subjected to the reaction conditions used for the preparation of Intermediate 6 to afford the title compound. HPLC/MS: 337.2 (M+1), $R_t$=0.94 min (LC-4 HPLC conditions).

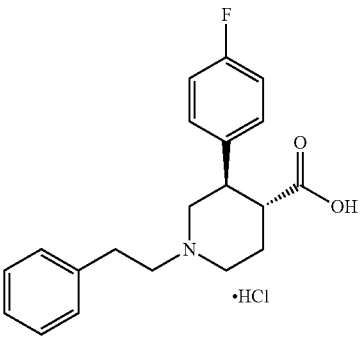

Intermediate 8

·HCl (3R*,4R*)-3-(4-fluorophenyl)-1-phenethyl-piperidine-4-carboxylic acid hydrochloride salt Step A: Methyl (3R*,4R*)-3-(4-fluorophenyl)piperidine-4-carboxylate hydrochloride salt (3R*,4R*)-1-tert-butoxycarbonyl-3-(4-fluorophenyl)piperidine-4-carboxylic acid (2.00 g, 6.19 mmol, prepared according to the procedure disclosed in WO 02/068387) in MeOH (20 ml) was treated dropwise with thionyl chloride (0.497 ml, 6.80 mmol) at rt. The mixture was stirred at rt for 12 h and then concentrated to afford the title compound. HPLC/MS: 238.0 (M+1); $R_t$=0.29 min.

Step B: Methyl (3R*,4R*)-3-(4-fluorophenyl)-1-phenethyl-piperidine-4-carboxylate The product from step A (770 mg, 2.81 mmol) in 1,2-dichloroethane (10 mL) was treated at rt with phenylacetaldehyde (0.987 mL, 8.44 mmol), sodium acetate (231 mg, 2.81 mmol) and sodium triacetoxyborohydride (1.79 g, 8.44 mmol). The mixture was stirred at rt for approximately 18 h, then poured into 1 M sodium hydroxide (10 mL) and extracted with ethyl acetate. The combined organic portions were dried with anhydrous sodium sulfate, filtered, and the filtrate was concentrated. The resulting residue was purified by column chromatography on SiO$_2$ (10% MeOH/methylene chloride) to afford the title compound. HPLC/MS: 342.3 (M+1); R$_t$=1.00 min (2 minute method).

Step C: (3R*,4R*)-3-(4-fluorophenyl)-1-phenethyl-piperidine-4-carboxylic acid

The product from step B (750 mg, 2.197 mmol) in THF (15 ml) was treated at rt with 1 M aqueous lithium hydroxide (4.83 ml, 4.83 mmol). The mixture was heated at 60° C. for approximately 12 h, then cooled to rt and concentrated. The resulting residue was treated with 2M aq HCl (4.40 mL) and lyophilized twice from water (5 mL) to afford the title compound. HPLC/MS: 328.2 (M+1); R$_t$=0.95 min (LC-2 HPLC conditions).

Example 1

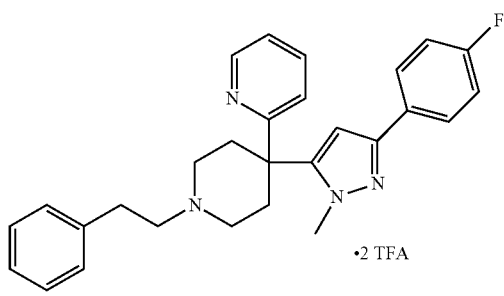 [SMILES: Cn1nc(-c2ccc(F)cc2)cc1C1(c2ccccn2)CCN(CCc2ccccc2)CC1 ; "·2 TFA"]

2-[4-[5-(4-fluorophenyl)-2-methyl-pyrazol-3-yl]-1-phenethyl-4-piperidyl]pyridine bis(trifluoroacetate) salt Intermediate 6 (11.6 mg, 0.028 mmol) in DMF (0.25 ml) was treated with 2-bromoethylbenzene (8.6 mg, 0.045 mmol) and potassium carbonate (7.83 mg, 0.57 mmol). The mixture was heated at 40° C. for 2 h, then diluted with a mixture of 1,4-dioxane and water (1:1 v/v, 3 ml) and directly purified by RP-HPLC(C18, acetonitrile, water, 0.1% TFA) to afford the title compound. HPLC/MS: 441.2 (M+1), R$_t$=1.73 min (LC-4 HPLC conditions).

Example 2

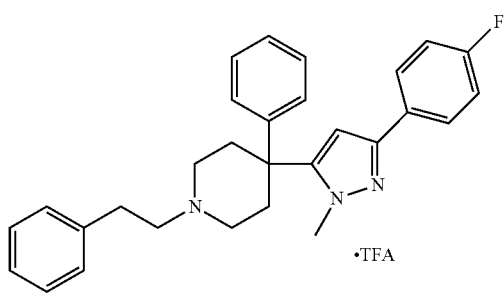 [SMILES: Cn1nc(-c2ccc(F)cc2)cc1C1(c2ccccc2)CCN(CCc2ccccc2)CC1 ; "·TFA"]

4-[5-(4-fluorophenyl)-2-methyl-pyrazol-3-yl]-1-phenethyl-4-phenyl-piperidine trifluoroacetate salt Example 2 was prepared according to the procedure of Example 1. HPLC/MS: 440.3 (M+1), R$_t$=1.92 min (LC-4 HPLC conditions).

Example 3

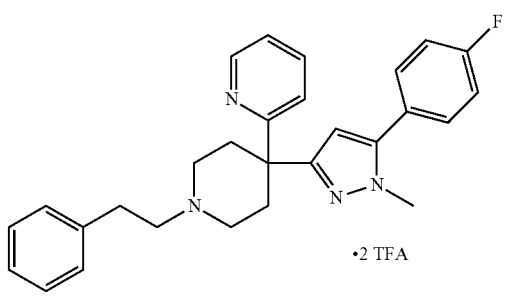 [SMILES: Cn1nc(C2(c3ccccn3)CCN(CCc3ccccc3)CC2)cc1-c1ccc(F)cc1 ; "·2 TFA"]

2-[4-[5-(4-fluorophenyl)-1-methyl-pyrazol-3-yl]-1-phenethyl-4-piperidyl]pyridine bis(trifluoroacetate) salt Intermediate 7 (19.3 mg, 0.047 mmol) in DMF (0.25 ml) was treated with 2-bromoethylbenzene (14.3 mg, 0.075 mmol) and potassium carbonate (7.83 mg, 0.57 mmol). The mixture was heated at 40° C. for 2 h, then diluted with a mixture of 1,4-dioxane and water (1:1 v/v, 3 ml) and directly purified by RP-HPLC(C18, acetonitrile, water, 0.1% TFA) to afford the title compound. HPLC/MS: 441.2 (M+1), R$_t$=1.66 min (LC-4 HPLC conditions).

Example 4

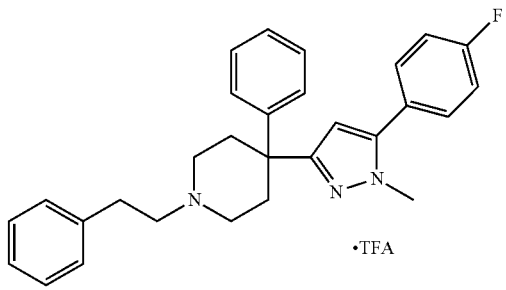 [SMILES: Cn1nc(C2(c3ccccc3)CCN(CCc3ccccc3)CC2)cc1-c1ccc(F)cc1 ; "·TFA"]

4-[5-(4-fluorophenyl)-1-methyl-pyrazol-3-yl]-1-phenethyl-4-phenyl-piperidine trifluoroacetate salt Example 4 was prepared according to the procedure of Example 3. HPLC/MS: 440.3 (M+1), R$_t$=1.96 min (LC-4 HPLC conditions).

Example 5

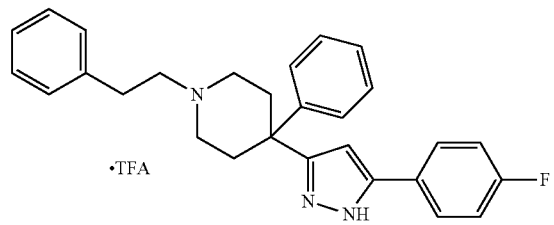 [SMILES: Fc1ccc(-c2cc(C3(c4ccccc4)CCN(CCc4ccccc4)CC3)n[nH]2)cc1]

4-[5-(4-fluorophenyl)-1H-pyrazol-3-yl]-1-phenethyl-4-phenyl-piperidine trifluoroacetate salt Example 5 was prepared according to the procedure of Example 3. HPLC/MS: 426.4 (M+1), $R_t$=1.65 min (LC-4 HPLC conditions).

Example 6

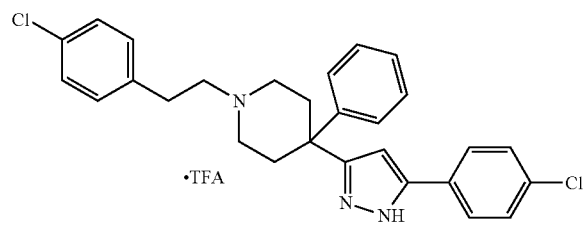 [SMILES: Clc1ccc(CCN2CCC(c3ccccc3)(c3cc(-c4ccc(Cl)cc4)[nH]n3)CC2)cc1]

1-[2-(4-chlorophenyl)ethyl]-4-[5-(4-chlorophenyl)-1H-pyrazol-3-yl]-4-phenyl-piperidine trifluoroacetate salt Example 6 was prepared according to the procedure of Example 3. HPLC/MS: 476.2 (M+1), $R_t$=2.05 min (LC-4 HPLC conditions).

Example 7

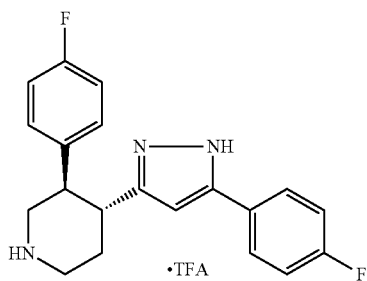 [SMILES: Fc1ccc(-c2cc([C@@H]3CCNC[C@H]3c3ccc(F)cc3)n[nH]2)cc1]

(3R,4R)-3-(4-fluorophenyl)-4-[5-(4-fluorophenyl)-1H-pyrazol-3-yl]piperidine trifluoroacetate salt The starting material (3R,4R)-1-tert-butoxycarbonyl-3-(4-fluorophenyl)piperidine-4-carboxylic acid was prepared as an enantiomeric mixture according to the procedure disclosed in WO 2002/068387. The resulting enantiomers were separated via SFC (Instrument: Berger MG II preparative SFC; Column: ChiralPak AD-H, 250×30 mm I.D.; Mobile phase: CO$_2$: Methanol (with 0.01% DEA), 95:5; Flow rate: 70 mL/min; Sample preparation: dissolved in Methanol, 20 mg/ml; Injection: 2 ml per injection.). The faster eluting enantiomer of (3R,4R)-1-tert-butoxycarbonyl-3-(4-fluorophenyl)piperidine-4-carboxylic acid (300 mg, 0.928 mmol) in THF (4.0 ml) was treated with CDT (165 mg, 1.021 mmol) and heated at 60° C. for 20 min. A solution of 4'-fluoroacetophenone (513 mg, 3.71 mmol) in a separate vial was treated at rt with solid lithium bis(trimethylsilyl)amide (621 mg, 3.71 mmol) and the mixture was stirred at rt for 10 min. This lithium mixture was then treated dropwise with the CDT-activated carboxylic acid solution. The combined mixture was stirred for 30 min at rt and then quenched with saturated aqueous NaHCO$_3$. The mixture was diluted with water and extracted with MTBE. The combined organic layers were dried with anhydrous Na$_2$SO$_4$, and then filtered. The filtrate was concentrated to give a residue. The residue was dissolved in EtOH, and treated with hydrazine (0.25 ml, 7.97 mmol). The reaction was heated at 60° C. for 1 h, then cooled to rt and concentrated. Purification of the resulting residue by chromatography on SiO$_2$ (0 to 10% MeOH/DCM) afforded tert-butyl (3R,4R)-3-(4-fluorophenyl)-4-[5-(4-fluorophenyl)-1H-pyrazol-3-yl]piperidine-1-carboxylate, which was dissolved in DCM (1 mL) and treated with TFA (1 mL), followed by stirring at rt for 12 h and concentrating under vacuum. Purification of the resulting residue by RP-HPLC (C18, 15% to 100% water/acetonitrile over 12 min, 0.1% TFA) afforded the title compound. HPLC/MS: 340.1 (M+1), R=1.45 min (LC-4 HPLC conditions). Racemic material can be obtained in a similar manner by using racemic starting material.

Example 8

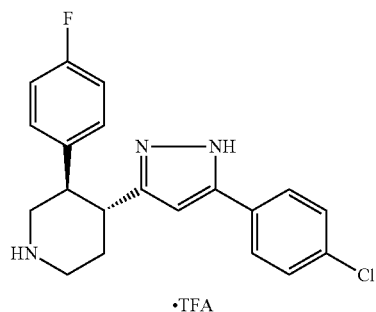 [SMILES: Fc1ccc([C@@H]2CNCC[C@H]2c2cc(-c3ccc(Cl)cc3)[nH]n2)cc1]

(3R*,4R*)-4-[5-(4-chlorophenyl)-1H-pyrazol-3-yl]-3-(4-fluorophenyl)piperidine trifluoroacetate salt Example 8 was prepared as a mixture of enantiomers according to the procedure of Example 7 starting from (3R*, 4R*)-1-tert-butyl-3-(4-fluorophenyl)piperidine-4-carboxylic acid hydrochloride salt, which was prepared according to the procedure disclosed in WO 2002/068387. HPLC/MS: 356.0, 357.9 (M+1), $R_t$=1.06 min (LC-2 HPLC conditions).

Examples 9 and 10

Example 9

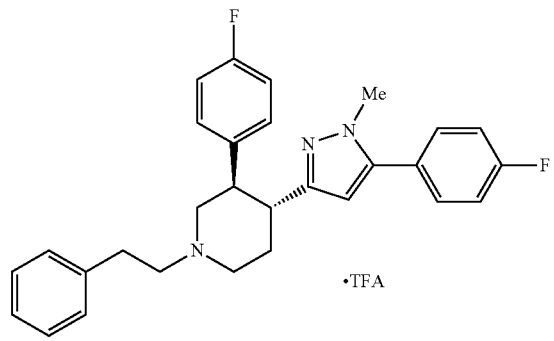

Example 10

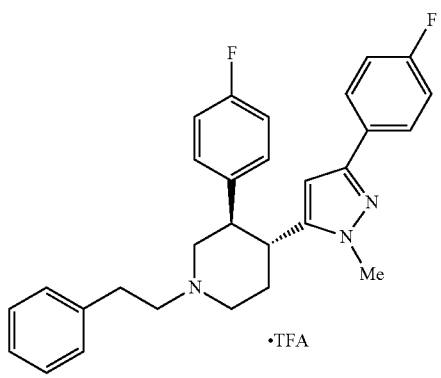

(3R,4R)-3-(4-fluorophenyl)-4-[5-(4-fluorophenyl)-1-methyl-pyrazol-3-yl]-1-phenethyl-piperidine trifluoroacetate salt and (3R,4R)-3-(4-fluorophenyl)-4-[5-(4-fluorophenyl)-2-methyl-pyrazol-3-yl]-1-phenethyl-piperidine trifluoroacetate salt Step A: (3R,4R)-3-(4-fluorophenyl)-4-[5-(4-fluorophenyl)-1-methyl-pyrazol-3-yl]piperidine trifluoroacetate salt and (3R,4R)-4-[5-(4-fluorophenyl)-2-methyl-pyrazol-3-yl]-3-(4-fluorophenyl)piperidine trifluoroacetate salt The title compounds of step A were prepared according to the procedure of Example 7 by substituting methyl hydrazine for hydrazine to afford a mixture of regioisomers. HPLC/MS: 354.1 (M+1), $R_t$=1.07 (LC-2 HPLC conditions).

Step B: (3R,4R)-3-(4-fluorophenyl)-4-[5-4-fluorophenyl)-1-methyl-pyrazol-3-yl]-1-phenethyl-piperidine trifluoroacetate salt and (3R,4R)-3-(4-fluorophenyl)-4-[5-(4-fluorophenyl)-2-methyl-pyrazol-3-yl]-1-phenethyl-piperidine trifluoroacetate salt The mixture of regioisomers from step A in acetonitrile (1.0 ml) was treated at rt with (2-bromoethyl)benzene (19.80 mg, 0.107 mmol) and potassium carbonate (37.0 mg, 0.267 mmol). The mixture was then stirred at rt for 24 h, and filtered. The filtrate was concentrated to give a residue. Purification of the residue by preparative TLC (5% MeOH/DCM) afforded the title compounds as separate regioisomers. Each regioisomer was further purified by RP-HPLC(C18, acetonitrile, water, 0.05% TFA) to afford (3R,4R)-3-(4-fluorophenyl)-4-[5-(4-fluorophenyl)-1-methyl-pyrazol-3-yl]-1-phenethyl-piperidine trifluoroacetate salt (the less polar regioisomer on SiO$_2$) HPLC/MS: 458.3 (M+1) $R_t$=1.76 min (LC-4 HPLC conditions); and (3R,4R)-3-(4-fluorophenyl)-4-[5-(4-fluorophenyl)-2-methyl-pyrazol-3-yl]-1-phenethyl-piperidine trifluoroacetate salt (the more polar regioisomer on SiO$_2$) HPLC/MS: 458.3 (M+1) $R_t$=1.81 (LC-4 HPLC conditions).

Example 11

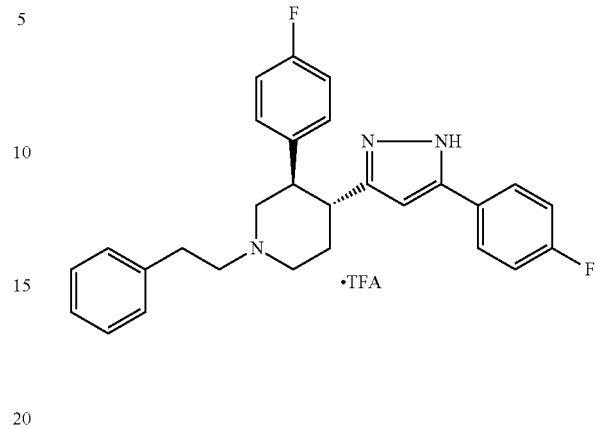

(3R*,4R*)-3-(4-fluorophenyl)-4-[5-(4-fluorophenyl)-1H-pyrazol-3-yl]-1-phenethyl-piperidine trifluoroacetate salt Intermediate 8 (50 mg, 0.137 mmol) in THF (2 mL) was treated with CDI (24.51 mg, 0.151 mmol), and heated at 60° C. for 20 min. A solution of 4t-fluoroacetone (76 mg, 0.550 mmol) in a separate vial was treated at rt with solid lithium bis(trimethylsilyl)amide (92 mg, 0.550 mmol), and stirred at rt for 10 min. This lithium mixture was then treated dropwise with the solution of the CDI-activated carboxylic acid. The resulting mixture was stirred for 30 min at rt and then treated with saturated aqueous NaHCO$_3$ (5 mL). The mixture was extracted with MTBE and the combined organic layers were dried (Na$_2$SO$_4$), and filtered. The filtrate was concentrated to give a residue. The residue was dissolved in EtOH and treated with hydrazine (0.25 ml, 7.97 mmol). The resulting mixture was then heated at 60° C. for 1 h, and concentrated to give a residue. The residue was purified by RP-HPLC(C18, water, acetonitrile, 0.05% TFA) to afford the title compound. HPLC/MS: 444.3 (M+1); $R_t$=1.72 min (LC-4 HPLC conditions).

Example 12

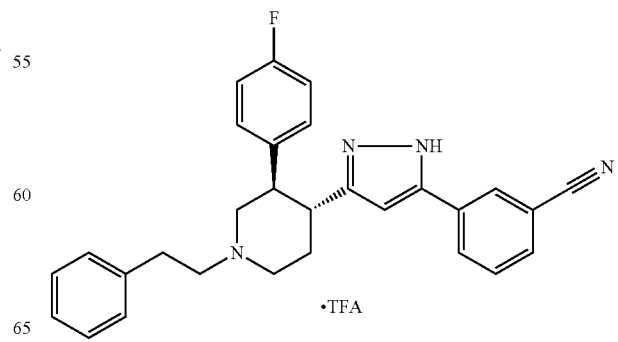

3-[3-[(3R*,4R*)-3-(4-fluorophenyl)-1-phenethyl-4-piperidyl]-1H-pyrazol-5-yl]benzonitrile triflizoroacetate salt Example 12 was prepared from Intermediate 8 according to the procedure of Example 11. HPLC/MS: 451.3 (M+1); R$_t$=1.10 min (LC-2 HPLC conditions).

Example 13

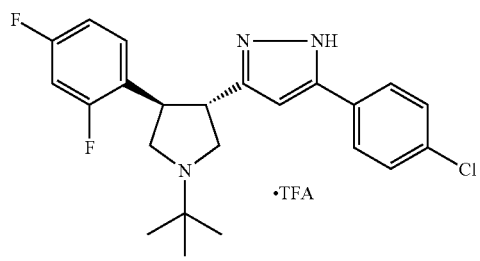 [SMILES: CC(C)(C)N1C[C@@H](c2cc(-c3ccc(Cl)cc3)[nH]n2)[C@H](c2ccc(F)cc2F)C1]

3-[(3S,4R)-1-tert-butyl-4-(2,4-difluorophenyl)pyrrolidin-3-yl]-5-(4-chlorophenyl)-1H-pyrazole trifluoroacetate salt Example 13 was prepared according to the procedure of Example 11 starting from (3S,4R)-1-tert-butyl-4-(2,4-difluorophenyl)-pyrrolidine-3-carboxylic acid, which was prepared according to the synthesis disclosed in WO 2007/015162. HPLC/MS: 416.1, 418.1 (M+1); R$_t$=1.70 min (LC-4 HPLC conditions).

Example 14

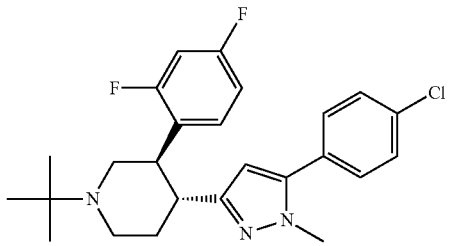 [SMILES: Cn1nc([C@@H]2CCN(C(C)(C)C)C[C@H]2c2ccc(F)cc2F)cc1-c1ccc(Cl)cc1]

(3R,4R)-1-tert-butyl-4-[5-(4-chlorophenyl)-1-methyl-pyrazol-3-yl]-3-(2,4-difluorophenyl)piperidine trifluoroacetate salt Example 14 was prepared according to the procedure of Example 13 starting from (3R,4R)-1-tert-butyl-3-(4-fluorophenyl)piperidine-4-carboxylic acid hydrochloride salt, which was prepared according to the procedure disclosed in WO 2002/068387. HPLC/MS: 444.1, 446.1 (M+1); R$_t$=1.12 min (LC-2 HPLC conditions).

Example 15

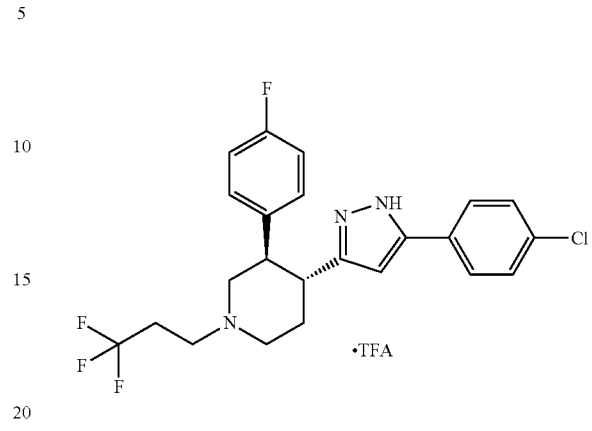

3R*,4R*)-4-[5-(4-chlorophenyl)-1H-pyrazol-3-yl]-3-(4-fluorophenyl)-1-(3,3,3-trifluoropropyppiperidine trifluoroacetate salt The product from Example 8 (10 mg, 0.021 mmol) and potassium carbonate (8.82 mg, 0.064 mmol) in acetonitrile (1.0 ml) were treated with 3-bromo-1,1,1-trifluoropropane (7.53 mg, 0.043 mmol) at rt. The reaction was heated at 60° C. After 24 h, additional 3-bromo-1,1,1-trifluoropropane (7.53 mg, 0.043 mmol) and potassium carbonate (8.82 mg, 0.064 mmol) were added. After a total of 36 h, the reaction mixture was filtered, and the filtrate was concentrated. Purification of the resulting residue by RP-HPLC (C18, acetonitrile, water, 0.05% TFA) afforded the title compound. HPLC/MS: 452.2, 454.1 (M+1); R$_t$=1.68 min (LC-4 HPLC conditions).

Example 16

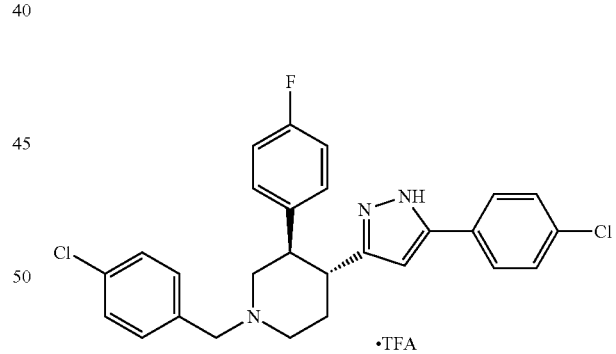

(3R*,4R*)-1-[(4-chlorophenyl)methyl]-4-[(5-(4-chlorophenyl)-1H-pyrazol-3-yl]-3-(4-fluorophenyl)piperidine trifluoroacetate salt The product from Example 8 (20 mg, 0.056 mmol), 4-chlorobenzaldehyde (11.85 mg, 0.084 mmol) and 4 Å molecular sieves (20 mg) in 1,2-dichloroethane (1.0 ml) were stirred at rt for 30 min. The reaction was then treated with sodium triacetoxyborohydride (23.82 mg, 0.112 mmol) and stirred for an additional 12 h at rt. Then the reaction mixture was treated with 2M aq NaOH (3 mL), stirred for 1 h at rt, and extracted with ethyl acetate. The combined organic layers were dried with anhydrous sodium sulfate, then filtered, and the filtrate was concentrated. The resulting residue was purified by RP-HPLC(C18, acetonitrile, water, 0.1% TFA) to afford the title compound. HPLC/MS: 480.0, 481.9 (M+1); R$_t$=1.81 min (LC-4 HPLC conditions).

Example 17

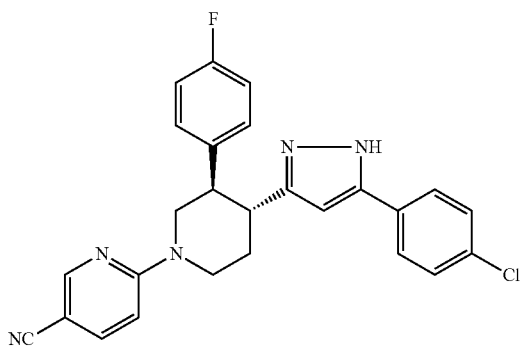 [SMILES: N#Cc1ccc(N2CC[C@@H](c3cc(-c4ccc(Cl)cc4)[nH]n3)[C@H](c3ccc(F)cc3)C2)nc1]

6-[(3R,4R)-4-[5-(4-chlorophenyl)-1H-pyrazol-3-yl]-3-(4-fluorophenyl)-1-piperidyl]pyridine-3-carbonitrile 3R,4R)-4-[5-(4-chlorophenyl)-1H-pyrazol-3-yl]-3-(4-fluorophenyppiperidine (25 mg, 0.053 mmol, prepared in a similar manner to Examples 7 and 8) in N-methyl-2-pyrrolidinone (0.9 ml) was treated with diisopropylethylamine (0.011 ml, 0.064 mmol) and 2-bromo-5-cyanopyridine (11.68 mg, 0.064 mmol). The mixture was heated in a microwave reactor at 150° C. for 30 min. Direct purification of the mixture by RP-HPLC(C18, acetonitrile, water, 0.05% TFA) afforded the title compound. HPLC/MS: 458.1, 460.0 (M+1); R$_t$=1.24 min (LC-2 HPLC conditions).

Example 18

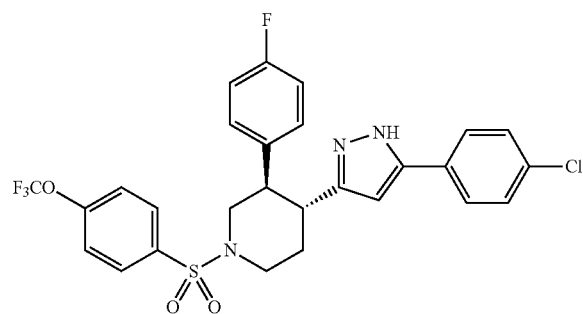 [SMILES: O=S(=O)(c1ccc(OC(F)(F)F)cc1)N1CC[C@@H](c2cc(-c3ccc(Cl)cc3)[nH]n2)[C@H](c2ccc(F)cc2)C1]

3R*,4R*)-4-[5-(4-chlorophenyl)-1H-pyrazol-3-yl]-3-(4-fluorophenyl)-1-[4-(trifluoromethoxy)phenyl]sulfonyl-piperidine The product from Example 8 (23 mg, 0.049 mmol) in pyridine (1.0 ml) was treated with 4-trifluoromethoxybenzenesulfonyl chloride (63.8 mg, 0.245 mmol). The reaction mixture was heated to 60° C. for 12 h. The mixture was then concentrated and purified by RP-HPLC(C18, acetonitrile, water, 0.05% TFA) to afford the title compound. HPLC/MS: 580.0, 582.1; R$_t$=2.33 min (LC-4 HPLC conditions).

Example 19

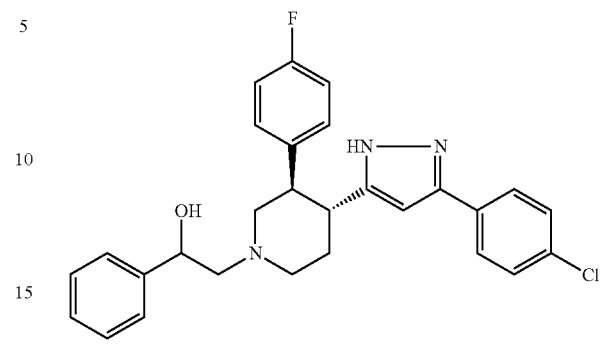

2[(3R,4R)-4-[3-(4-chlorophenyl)-1H-pyrazol-5-yl]-3-(4-fluorophenyl)-1-piperidyl]-1-phenyl-ethanol Step A: 2-[(3R,4R)-4-[3-(4-chlorophenyl)-1H-pyrazol-5-yl]-3-(4-fluorophenyl)-1-piperidyl]-1-phenyl-ethanone (3R,4R)-4-[5-(4-chlorophenyl)-1H-pyrazol-3-yl]-3-(4-fluorophenyl)piperidine (100 mg, 0.213 mmol, prepared in a similar manner to Examples 7 and 8), 2-bromoaceto-phenone (50.8 mg, 0.255 mmol) and potassium carbonate (147 mg, 1.064 mmol) in acetonitrile (1.0 ml) was stirred at rt for 4 h. Direct purification of the crude reaction mixture by RP-HPLC (C18, acetonitrile, water, 0.1% TFA) afforded the title compound. HPLC/MS: 474.3, 476.3 (M+1); R$_t$=1.74 min (LC-4 HPLC conditions).

Step B: 2-[3R,4R)-4-[3-(4-chlorophenyl)-1H-pyrazol-5-yl]-3-(4-fluorophenyl)-1-piperidyl]-1-phenyl-ethano The product from step A (40 mg, 0.084 mmol) in ethanol (1.0 ml) was treated at rt with sodium borohydride (31.9 mg, 0.844 mmol). The mixture was stirred at rt for 16 h, then quenched with 2M aq NaOH (0.1 mL) and concentrated. Direct purification of the residue by RP-HPLC(C18, acetonitrile, water, 0.1% TFA) afforded the title compound. HPLC/MS: 476.3, 478.3 (M+1); R$_t$=1.66 min (LC-4 HPLC conditions).

Example 20

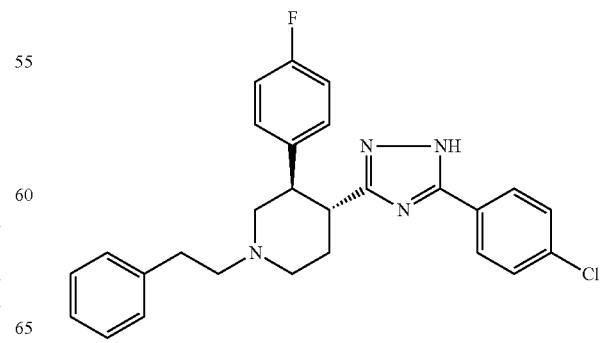

(3R*,4R*)-4-[5-(4-chlorophenyl)-1H-1,2,4-triazol-3-yl]-3-(4-fluorophenyl)-1-phenethyl-piperidine trifluoroacetate salt Step A: (3R*,4R*)—N-(4-chlorobenzenecarbothioyl)-3-(4-fluorophenyl)-1-phenethyl-piperidine-4-carboxamide A mixture of (3R*,4R*)-3-(4-fluorophenyl)-1-phenethyl-piperidine-4-carboxylic acid (50 mg, 0.137 mmol, prepared according to the procedure disclosed in WO 2002/068387) and 4-chlorothiobenzamide (28.3 mg, 0.165 mmol) in $CH_2Cl_2$ (1.0 ml) was treated with HBTU (62.5 mg, 0.165 mmol) and DMAP (10 mg, 0.082 mmol) at rt. The mixture was stirred at rt for 6 h and then concentrated. The resulting residue was purified by RP-HPLC(C18, water, acetonitrile, 0.05% TFA) to afford the title compound, which was contaminated with 4-chlorothiobenzamide and was used in the next step without further purification. HPLC/MS: 481.3, 483.1 (M+1); $R_t$=1.14 (LC-2 HPLC conditions).

Step B: 3R*,4R*)-4-[5-(4-chlorophenyl)-1H-1,2,4-triazol-3-yl]-3-(4-fluorophenyl)-1-phenethyl-piperidine The product from step A was dissolved in glacial acetic acid (1 ml) and dioxane (1 ml) and treated with sodium acetate (13.53 mg, 0.165 mmol) and hydrazine (5.18 μl, 0.165 mmol). The reaction mixture was heated in a microwave at 90° C. for 30 min. The mixture was then directly purified by RP-HPLC(C18, acetonitrile, water, 0.05% TFA) to afford the title compound. HPLC/MS: 461.3, 463.2; $R_t$=1.68 (LC-4 HPLC conditions).

The compounds in Table 1 were prepared according to the procedures of Examples 1-6, starting from the appropriate starting materials.

TABLE 1

| Example Number | Compound Name | $R^1$ | $R^3$ | $R^5$ | MW/ MS: M + 1 | $R_t$ (min) LC-4 HPLC conditions |
|---|---|---|---|---|---|---|
| 21 | 1-phenethyl-4-(5-phenethyl-1H-pyrazol-3-yl)-4-phenyl-piperidin-1-ium trifluoroacetate salt | phenethyl | phenyl | phenethyl | 435.6/ 436.4 | 1.72 |
| 22 | 3-[3-(1-phenethyl-4-phenyl-piperidin-1-ium-4-yl)-1H-pyrazol-5-yl]benzonitrile trifluoroacetate salt | phenethyl | phenyl | 3-cyanophenyl | 432.6/ 433.2 | 1.66 |
| 23 | 1-[2-(4-chlorophenyl)ethyl]-4-[5-(4-chlorophenyl)-1H-pyrazol-3-yl]-4-methyl-piperidin-1-ium trifluoroacetate salt | 2-(4-chlorophenyl)ethyl | $CH_3$ | 4-chlorophenyl | 414.38/ 414.21 | 1.92 |
| 24 | 1-[2-(4-chlorophenyl)ethyl]-4-[5-(4-chlorophenyl)-1H-pyrazol-3-yl]-4-ethyl-piperidin-1-ium trifluoroacetate salt | 2-(4-chlorophenyl)ethyl | $CH_3CH_2$ | 4-chlorophenyl | 428.41/ 428.88 | 1.98 |
| 25 | 4-[5-(4-chlorophenyl)-1H-pyrazol-3-yl]-1-phenethyl-4-phenyl-piperidin-1-ium trifluoroacetate salt | phenethyl | phenyl | 4-chlorophenyl | 442.01/ 442.16 | 1.83 |

TABLE 1-continued

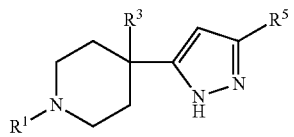

| Example Number | Compound Name | R¹ | R³ | R⁵ | MW/ MS: M + 1 | R$_t$ (min) LC-4 HPLC conditions |
|---|---|---|---|---|---|---|
| 26 | 1-phenethyl-4-phenyl-4-(5-phenyl-1H-pyrazol-3-yl)piperidin-1-ium; trifluoroacetate salt | 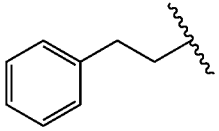 [SMILES: *CCc1ccccc1] | 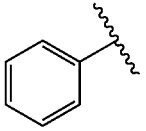 [SMILES: *c1ccccc1] | 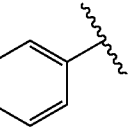 | 407.56/ 408.40 | 1.82 |

The compounds in Table 2 were prepared according to the procedures of Examples 7, 8, 11, 12, 14, 15, 16, 17, 18, and 19, starting from the appropriate starting materials.

TABLE 2

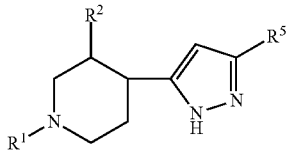

| Example Number | Compound name | R¹ | R² | R⁵ | MW | M + 1 | R$_t$ (HPLC method) |
|---|---|---|---|---|---|---|---|
| 27 | (3R*,4R*)-1-[2-(4-chlorophenyl)ethyl]-4-[5-(4-chlorophenyl)-1H-pyrazol-3-yl]-3-(4-fluorophenyl)piperidin-1-ium trifluoroacetate | 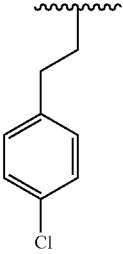 [SMILES: *CCc1ccc(Cl)cc1] | 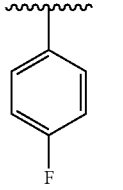 | 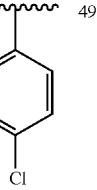 | 494.4 | 494.0, 496.0 | 1.16 min (LC-2) |
| 28 | tert-butyl 4-[(3R*,4R*)-4-[5-(4-chlorophenyl)-1H-pyrazol-3-yl]-3-(4-fluorophenyl)piperidin-1-ium-1-yl]piperidine-1-carboxylate trifluoroacetate salt | 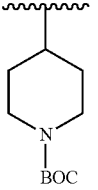 [SMILES: *C1CCN(C(=O)OC(C)(C)C)CC1] | 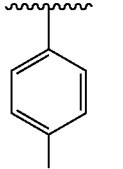 | 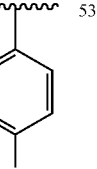 | 539.1 | 539.2, 540.9 | 1.06 min (LC-2) |
| 29 | 2-[(3R*,4R*)-4-[5-(4-chlorophenyl)-1H-pyrazol-3-yl]-3-(4-fluorophenyl)piperidin-1-ium-1-yl]-5-(trifluoromethyl)pyridine trifluoroacetate salt | 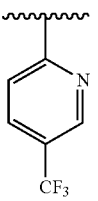 | 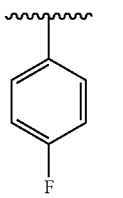 [SMILES: *c1ccc(F)cc1] | 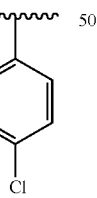 | 500.9 | 501.0, 503.0 | 2.37 min (LC-4) |

TABLE 2-continued

| Example Number | Compound name | R¹ | R² | R⁵ | MW | M + 1 | R_t (HPLC method) |
|---|---|---|---|---|---|---|---|
| 30 | (3R,4R)-1-tert-butyl-4-[5-(4-chlorophenyl)-1H-pyrazol-3-yl]-3-(2,4-difluorophenyl)piperidin-1-ium trifluoroacetate salt | tert-butyl | 2,4-difluorophenyl | 4-chlorophenyl | 429.9 | 430.1, 432.0 | 1.10 min (LC-2) |
| 31 | (3S,4S)-4-[5-(4-chlorophenyl)-1H-pyrazol-3-yl]-3-(4-fluorophenyl)-1-phenethyl-piperidin-1-ium trifluoroacetate salt | phenethyl | 4-fluorophenyl | 4-chlorophenyl | 460.0 | 460.3, 462.3 | 1.77 (LC-4) |
| 32 | (3R,4R)-4-[5-(4-chlorophenyl)-1H-pyrazol-3-yl]-3-(4-fluorophenyl)-1-phenethyl-piperidin-1-ium trifluoroacetate salt | phenethyl | 4-fluorophenyl | 4-chlorophenyl | 460.0 | 460.3, 462.3 | 1.83 (LC-4) |
| 33 | 2-[[(3R*,4R*)-4-[5-(4-chlorophenyl)-1H-pyrazol-3-yl]-3-(4-fluorophenyl)piperidin-1-ium-1-yl]methyl]pyridin-1-ium; bis(trifluoroacetate) salt | (pyridin-2-yl)methyl | 4-fluorophenyl | 4-chlorophenyl | 447.0 | 447.1, 449.0 | 1.09 (LC-2) |
| 34 | 4-chlorophenyl)-1H-pyrazol-3-yl]-1-(2,2-dimethylpropyl)-3-(4-fluorophenyl)piperidin-1-ium trifluoroacetate salt | 2,2-dimethylpropyl | 4-fluorophenyl | 4-chlorophenyl | 426.0 | 426.1, 428.1 | 1.68 min (4 min) |
| 35 | (3R*,4R*)-4-[5-(4-chlorophenyl)-1H-pyrazol-3-yl]-3-(4-fluorophenyl)-1-isopropyl-piperidin-1-ium trifluoroacetate salt | isopropyl | 4-fluorophenyl | 4-chlorophenyl | 397.9 | 398.1, 400.0 | 1.55 min (LC-4) |

TABLE 2-continued

[Structure: piperidine with R¹ on N, R² at 4-position, connected to pyrazole with R⁵]

| Example Number | Compound name | R¹ | R² | R⁵ | MW | M + 1 | R_t (HPLC method) |
|---|---|---|---|---|---|---|---|
| 36 | (3R*,4R*)-4-[5-(4-chlorophenyl)-1H-pyrazol-3-yl]-3-(4-fluorophenyl)-1-(2,2,2-trifluoroethyl)piperidin-1-ium trifluoroacetate salt | -CH₂CF₃ | 4-fluorophenyl | 4-chlorophenyl | 437.9 | 438.3, 440.2 | 1.99 min (LC-4) |

The compounds in Table 3 were prepared according to the procedures of Examples 8, 9, 10 and 13 starting from (3S, 4R)-1-tert-butoxycarbonyl-4-(2,4-difluorophenyl)pyrrolidine-3-carboxylic acid, which was prepared according to the procedure disclosed in WO 2007/015157.

TABLE 3

[Structure: pyrrolidine with R¹ on N, R² at 4-position, connected to pyrazole with R⁵]

| Example Number | Compound name | R¹ | R² | R⁵ | MW | M + 1 | R_t (HPLC method) |
|---|---|---|---|---|---|---|---|
| 37 | 3-[(3S,4R)-4-(2,4-difluorophenyl)pyrrolidin-1-ium-3-yl]-5-(4-fluorophenyl)-1H-pyrazole trifluoroacetate salt | H | 2,4-difluorophenyl | 4-fluorophenyl | 343.4 | 344.0 | 1.40 min (LC-4) |
| 38 | 3-[(3S,4R)-1-benzyl-4-(2,4-difluorophenyl)pyrrolidin-1-ium-3-yl]-5-(4-fluorophenyl)-1H-pyrazole trifluoroacetate | benzyl | 2,4-difluorophenyl | 4-fluorophenyl | 433.5 | 434.3 | 1.66 min (LC-4) |
| 39 | 3-[(3S,4R)-4-(2,4-difluorophenyl)-1-phenethyl-pyrrolidin-1-ium-3-yl]-5-(4-fluorophenyl)-1H-pyrazole trifluoroacetate | phenethyl | 2,4-difluorophenyl | 4-fluorophenyl | 447.5 | 448.3 | 1.73 min (LC-4) |

The utility of the compounds in accordance with the present invention as inhibitors of prolylcarboxypeptidase (PRCP) enzyme activity may be demonstrated by the following assays:

Biological Example 1

Prolylcarboxypeptidase (PRCP) Enzyme Activity Assay

The potency of compounds of formula I against PrCP was determined by a fluorescence intensity kinetic assay measuring the $IC_{50}$ values of PrCP inhibitor test compounds. Recombinant human and mouse PrCP enzymes from CHO or HEK expression systems (with comparable results for HEK enzymes) were prepared in-house and used in the assay. The assay was run on a Perkin. Elmer Envision 2103 plate reader using a 320 nm excitation filter and a 405 emission filter. The assay was performed using a Hamilton Star liquid handling workstation. The assay employed the internally quenched fluorescent substrate (1S)-1-carboxy-5-[(2,4-dinitrophenyl)amino]pentyl [(7-methoxy-2-oxo-2H-chromen-4-yl)acetyl]-L-alanyl-L-prolinate prepared in house. The assay was run in a 384-well microtiter plate at 37° C. with a total volume of 50 uL. Final assay concentrations were 0.13 nM human PrCP (CHO) or 0.09 nM mouse PrCP (CHO) enzyme, 15 uM substrate and varying concentrations of inhibitor in buffer containing 10 mM NaOAc, 100 mM NaCl and 19.5 ug/mL BSA at pH 5.5. The assay also contained 2% DMSO used to solubilize the substrate and inhibitor. Inhibitors were prepared in 100% DMSO and serial diluted (in 100% DMSO) to generate 11 point titration curves. Either 39 uL of human or mouse PrCP enzyme was added to the wells of the assay plate, followed by a 1 uL addition of the serially diluted inhibitor and mixed three times using a 30 uL mix volume. The reaction was initiated by the addition of 10 uL substrate and mixed three times using a 30 uL mix volume. The reactions were monitored continuously over 25 min at 37° C. to obtain initial velocities. IC50 values were calculated by comparing the resulting rates of reaction of the inhibited and control initial velocities. For the more potent compounds, a modified dilution series at a lower concentration range was used to more accurately determine the potency.

The enzymes were diluted in a mixture of 10 mM NaOAc (pH 5.5)/100 mM NaCl buffer containing 25 ug/mL bovine serum albumin that had been warmed to 37° C. in a water bath. The PrCP inhibitor test compounds were plated in 100% DMSO with a highest concentration of 500 uM. There were 12 dilution points for each compound tested including a blank with DMSO only. The test compounds from the source titration plate were transferred into the assay reaction plate at a 1:50 dilution using the Hamilton Star workstation and mixed, resulting in a final concentration for the test compounds in the range of 10,000 to 0.066 nM. Likewise, two control compounds were similarly titrated and included in each assay, with final starting concentrations starting at 10,000 nM and 200 nM, respectively. The reaction was initiated by the addition of 75 uM of the (1S)-1-carboxy-5-[(2,4-dinitrophenyl)amino]pentyl N-[(7-methoxy-2-oxo-2H-chromen-4-yl)acetyl]-L-alanyl-L-prolinate substrate, which was diluted in a mixture of 10 mM NaOAc (pH 5.5)/100 mM NaCl that had been warmed to 37° C. in a water bath, dispensed using the Hamilton Star workstation and mixed. The substrate was solubilized in 100% DMSO prior to dilution into the assay. The final assay concentrations in the 50 uL reactions were 15 uM of (1S)-1-carboxy-5-[(2,4-dinitrophenyl)amino]pentyl N-[(7-methoxy-2-oxo-2H-chromen-4-yl)acetyl]-L-alanyl-L-prolinate substrate, 0.13 nM Human PrCP (CHO) or 0.09 nM Mouse PrCP (CHO), and 2% DMSO.

The compounds of the present invention, including the compounds of Examples 1 to 39, exhibit a PrCP inhibition constant $IC_{50}$ of less than 10 μM. Preferred compounds of the present invention were found to exhibit a PRCP inhibition constant $IC_{50}$ of less than 1 μM. More preferred compounds of the present invention were found to exhibit a PrCP inhibition constant $IC_{50}$ of less than 100 nM.

| Human PRCP Enzyme Inhibition for Selected Compounds | | |
|---|---|---|
| Example Number | $IC_{50}$ (nM) | Cell line |
| Example 1 | 3.3 | CHO |
| Example 2 | 7.0 | CHO |
| Example 3 | 498 | CHO |
| Example 5 | 29.8 | HEK |
| Example 6 | 175 | HEK |
| Example 11 | 2.3 | CHO |
| Example 12 | 7.9 | CHO |
| Example 16 | 153.5 | HEK |
| Example 13 | 413 | HEK |
| Example 20 | 50.9 | CHO |

Examples of Pharmaceutical Compositions

As a specific embodiment of an oral composition of a composition of the present invention, 5 mg of Example 1 is formulated with sufficient finely divided lactose to provide a total amount of 580 to 590 mg to fill a size 0 hard gelatin capsule.

As another specific embodiment of an oral composition of a compound of the present invention, 2.5 mg of Example 1 is formulated with sufficient finely divided lactose to provide a total amount of 580 to 590 mg to fill a size 0 hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the practices of the present invention. It is intended, therefore, that the invention be limited only by the scope of the claims which follow and that such claims be interpreted as broadly as is reasonable.

What is claimed is:

1. A compound of structural formula I-1 or I-2:

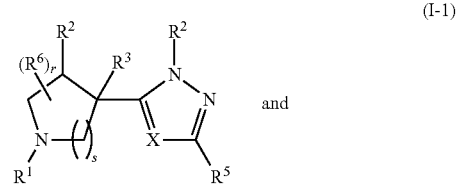

-continued

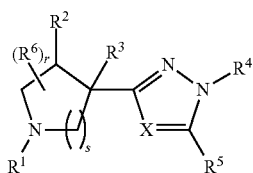

(I-2)

or a pharmaceutically acceptable salt thereof; wherein
X is CH or N;
each $R^1$ is independently selected from the group consisting of:
(1) —$C_{1-6}$ alkyl,
(2) —$(CH_2)_m$—C(O)-aryl,
(3) —$(CH_2)_m$—CH(OH)—$(CH_2)_p$-aryl,
(4) —$(CH_2)_m$—$SO_2$-aryl,
(5) —$(CH_2)_m C_{2-6}$cycloheteroalkyl,
(6) —$(CH_2)_m$ aryl, and
(7) —$(CH_2)_m$ heteroaryl,
wherein each $CH_2$, alkyl, cycloheteroalkyl, aryl and heteroaryl is unsubstituted or substituted with one to three groups independently selected from $R^a$;
each $R^2$ is selected from the group consisting of:
(1) hydrogen, and
(2) —$(CH_2)_n$ aryl,
wherein each $CH_2$, and aryl is unsubstituted or substituted with one or two substituents selected from $R^b$;
each $R^3$ is independently selected from the group consisting of:
(1) hydrogen,
(2) -aryl, and
(3) -heteroaryl,
wherein each aryl and heteroaryl is unsubstituted or substituted with one to three substituents selected from $R^c$,
provided that at least one of $R^2$ and $R^3$ is not hydrogen;
each $R^4$ is independently selected from the group consisting of:
(1) hydrogen, and
(2) —$C_{1-6}$ alkyl,
wherein alkyl is unsubstituted or substituted with hydroxy or one to three halogens;
each $R^5$ is independently selected from the group consisting of:
(1) hydrogen,
(2) —$C_{1-6}$ alkyl,
(3) —$C_{1-6}$ alkoxy,
(4) —$CF_3$,
(5) —$(CH_2)_t C_{3-7}$cycloalkyl,
(6) —$(CH_2)_t C_{2-6}$cycloheteroalkyl,
(7) —$(CH_2)_t$ aryl, and
(8) —$(CH_2)_t$ heteroaryl,
wherein each $CH_2$, alkyl, alkoxy, cycloalkyl, cycloheteroalkyl, aryl and heteroaryl is unsubstituted or substituted with one to three substituents selected from $R^d$;
each $R^6$ is independently selected from the group consisting of:
(1) hydrogen,
(2) halogen,
(3) —$CF_3$, and
(4) —$C_{1-6}$ alkyl,
wherein alkyl is unsubstituted or substituted with hydroxy or one to three halogens;

each $R^a$ is independently selected from the group consisting of:
(1) hydrogen,
(2) oxo,
(3) halogen,
(4) —$C_{1-4}$alkyl,
(5) —$OC_{1-4}$alkyl,
(6) —$CF_3$,
(7) —OH,
(8) —$OCF_3$,
(9) —CN, and
(10) —$CO_2$—$C_{1-6}$alkyl;
each $R^b$ is independently selected from the group consisting of:
(1) hydrogen,
(2) halogen,
(3) —$C_{1-4}$alkyl,
(4) —$OC_{1-4}$alkyl,
(5) —$CF_3$,
(6) —$OCF_3$,
(7) —CN, and
(8) —$CO_2$—$C_{1-6}$alkyl;
$R^c$ is independently selected from the group consisting of:
(1) hydrogen,
(2) halogen,
(3) —$C_{1-4}$alkyl,
(4) —$OC_{1-4}$alkyl,
(5) —$CF_3$,
(6) —$OCF_3$,
(7) —CN, and
(8) —$CO_2$—$C_{1-6}$alkyl;
each $R^d$ is independently selected from the group consisting of:
(1) hydrogen,
(2) halogen,
(3) —$C_{1-4}$alkyl,
(4) —$OC_{1-4}$alkyl,
(5) —$CF_3$,
(6) —$OCF_3$,
(7) —CN, and
(8) —$CO_2$—$C_{1-6}$alkyl;
m is selected from 0, 1, 2 and 3;
n is selected from 0, 1, 2, and 3;
p is selected from 0, 1, 2 and 3;
r is selected from 0, 1, and 2;
s is selected from 1 and 2; and
t is selected from 0, 1, 2 and 3.

2. The compound of claim 1 wherein each $R^1$ is independently selected from the group consisting of:
(1) —$C_{1-6}$ alkyl, and
(2) —$(CH_2)_m$ phenyl,
wherein each $CH_2$, alkyl and phenyl is unsubstituted or substituted with one to three groups independently selected from $R^a$; or a pharmaceutically acceptable salt thereof.

3. The compound of claim 1 wherein $R^2$ is selected from the group consisting of:
(1) hydrogen, and
(2) -phenyl,
wherein each phenyl is unsubstituted or substituted with one or two substituents selected from $R^b$; or a pharmaceutically acceptable salt thereof.

4. The compound of claim 1 wherein $R^3$ is selected from the group consisting of:
(1) hydrogen,
(2) -phenyl, and
(3) -pyridine,
wherein each phenyl and pyridine is unsubstituted or substituted with one to three substituents selected from Re, provided that at least one of $R^2$ and $R^3$ is not hydrogen;
or a pharmaceutically acceptable salt thereof.

5. The compound of claim 1 wherein $R^5$ is —$(CH_2)_t$ phenyl, wherein each $CH_2$ and phenyl is unsubstituted or substituted with one to three substituents selected from $R^d$; or a pharmaceutically acceptable salt thereof.

6. The compound of claim 5 wherein $R^5$ is selected from the group consisting of:
(1) —$(CH_2)_2$-phenyl, and
(2) -phenyl,
wherein each $CH_2$ and phenyl is unsubstituted or substituted with one to three substituents selected from $R^d$; or a pharmaceutically acceptable salt thereof.

7. The compound of claim 1 wherein $R^6$ is hydrogen; or a pharmaceutically acceptable salt thereof.

8. The compound of claim 1 wherein r is 0, and s is 1; or a pharmaceutically acceptable salt thereof.

9. The compound of claim 1 wherein r is 0, and s is 2; or a pharmaceutically acceptable salt thereof.

10. The compound of claim 1 wherein
each $R^1$ is independently selected from the group consisting of:
(1) —$C_{1-6}$ alkyl,
(2) —$(CH_2)_m$—C(O)-aryl,
(3) —$(CH_2)_m$—CH(OH)—$(CH_2)_p$-aryl,
(4) —$(CH_2)_m$—$SO_2$-aryl,
(5) —$(CH_2)_m$ $C_{2-6}$cycloheteroalkyl,
(6) —$(CH_2)_m$ aryl, and
(7) —$(CH_2)_m$ heteroaryl,
wherein each $CH_2$, alkyl, cycloheteroalkyl, aryl and heteroaryl is unsubstituted or substituted with one to three groups independently selected from $R^a$;
$R^2$ is selected from the group consisting of:
(1) hydrogen, and
(2) —$(CH_2)_n$ aryl,
wherein each $CH_2$ and aryl is unsubstituted or substituted with one or two substituents selected from $R^b$;
each R3 is independently selected from the group consisting of:
(1) hydrogen,
(2) -aryl, and
(3) -heteroaryl,
wherein each aryl and heteroaryl is unsubstituted or substituted with one to three substituents selected from $R^c$, provided that at least one of $R^2$ and $R^3$ is not hydrogen;
$R^5$ is —$(CH_2)_t$ phenyl, wherein each $CH_2$ and phenyl is unsubstituted or substituted with one to three substituents selected from $R^d$;
$R^6$ is hydrogen; and
m is 0, 1 or 2;
n is 0 or 1;
p is 0 or 1; and
t is 0 or 2;
or a pharmaceutically acceptable salt thereof.

11. The compound of claim 1 wherein:
$R^1$ is independently selected from the group consisting of:
(1) —$C_{1-6}$ alkyl, and
(2) —$(CH_2)_m$ phenyl,
wherein each $CH_2$, alkyl and phenyl is unsubstituted or substituted with one to three groups independently selected from $R^a$;
$R^2$ is selected from the group consisting of:
(1) hydrogen, and
(2) -phenyl,
wherein each phenyl is unsubstituted or substituted with one or two substituents selected from $R^b$;
$R^3$ is selected from the group consisting of:
(1) hydrogen,
(2) -phenyl, and
(3) -pyridine,
wherein each phenyl and pyridine is unsubstituted or substituted with one to three substituents selected from $R^c$, provided that at least one of $R^2$ and $R^3$ is not hydrogen;
$R^5$ is -phenyl, wherein phenyl is unsubstituted or substituted with one to three substituents selected from $R^d$;
$R^6$ is hydrogen; and
m is 2;
or a pharmaceutically acceptable salt thereof.

12. A compound selected from the group consisting of:

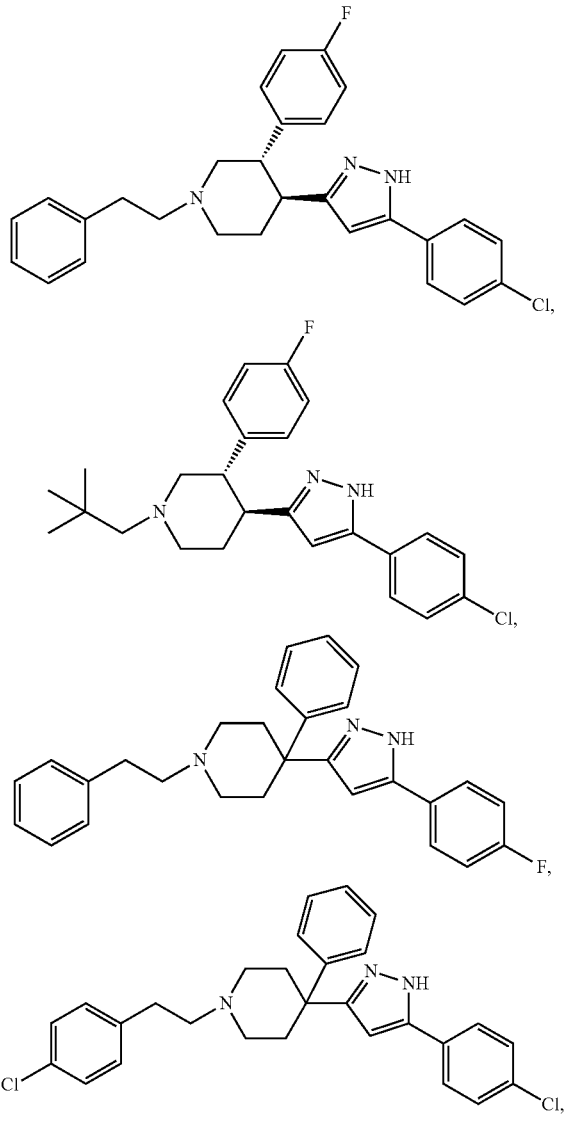

-continued

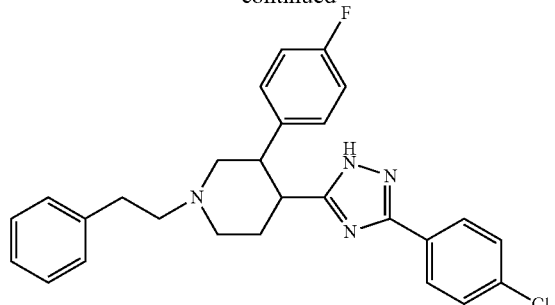

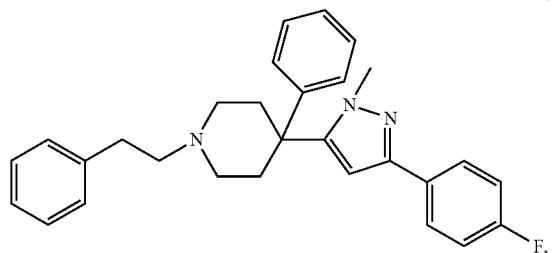

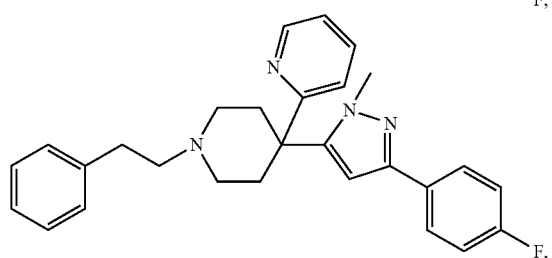

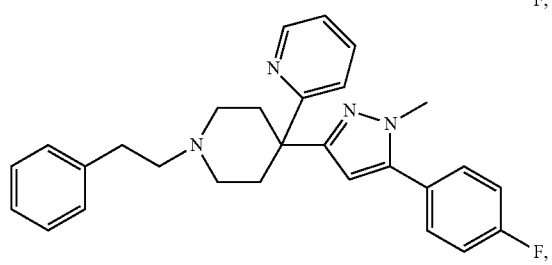

-continued

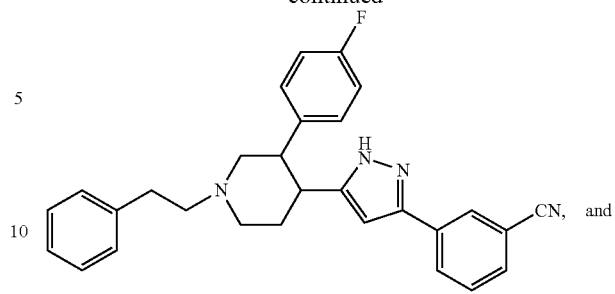

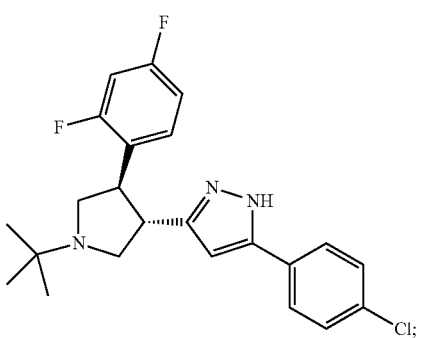

or a pharmaceutically acceptable salt thereof.

13. A pharmaceutical composition comprising a compound of claim 1 in combination with a pharmaceutically acceptable carrier.

14. A composition comprising a compound according to claim 1 and a compound selected from simvastatin, ezetimibe, taranabant and sitagliptin; and a pharmaceutically acceptable carrier.

* * * * *